(12) United States Patent
Gurtner et al.

(10) Patent No.: US 8,197,499 B2
(45) Date of Patent: *Jun. 12, 2012

(54) COMPOSITIONS AND METHODS FOR JOINING NON-CONJOINED LUMENS

(75) Inventors: Geoffrey C. Gurtner, Stanford, CA (US); Gerald G. Fuller, Stanford, CA (US); Michael T. Longaker, Atherton, CA (US); Jayakumar Rajadas, Cupertino, CA (US); Gordon Saul, Palo Alto, CA (US); C. Travis Rappleye, San Jose, CA (US); Evgenia Mandrusov, Santa Clara, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 468 days.

This patent is subject to a terminal disclaimer.

(21) Appl. No.: 12/340,588

(22) Filed: Dec. 19, 2008

(65) Prior Publication Data

US 2009/0187199 A1 Jul. 23, 2009

Related U.S. Application Data

(63) Continuation-in-part of application No. 11/962,077, filed on Dec. 20, 2007, which is a continuation-in-part of application No. 11/766,779, filed on Jun. 21, 2007.

(60) Provisional application No. 60/805,425, filed on Jun. 21, 2006, provisional application No. 60/806,242, filed on Jun. 29, 2006, provisional application No. 60/914,635, filed on Apr. 27, 2007.

(51) Int. Cl.
*A61B 17/08* (2006.01)

(52) U.S. Cl. .................................. 606/153; 606/154
(58) Field of Classification Search .................. 606/153, 606/214–215, 154
See application file for complete search history.

(56) References Cited

U.S. PATENT DOCUMENTS

| | | | |
|---|---|---|---|
| 3,683,926 A * | 8/1972 | Suzuki | 606/154 |
| 3,740,421 A | 6/1973 | Schmolka et al. | |
| 4,035,334 A | 7/1977 | Davydov et al. | |
| 4,657,019 A | 4/1987 | Walsh et al. | |
| 4,770,176 A | 9/1988 | McGreevy et al. | |
| 5,141,516 A | 8/1992 | Detweiler | |

(Continued)

FOREIGN PATENT DOCUMENTS

CN 1377706 11/2002

(Continued)

OTHER PUBLICATIONS

Escobar-Chavez et al., "Applications of Thermo-Reversible Pluronic F-128 Gels in Pharmaceutical Formulations," J. Pharm Pharmaceut. Sci. (www.csps Canada.org), vol. 9, No. 3, pp. 339-358 (2006).

(Continued)

*Primary Examiner* — Darwin Erezo
*Assistant Examiner* — Gregory Anderson
(74) *Attorney, Agent, or Firm* — Foley & Lardner LLP

(57) ABSTRACT

Disclosed are compositions, methods, and kits for joining together non-conjoined lumens in a patient's body including vascular lumens. More particularly, in various aspects, this invention provides compositions, methods, and kits for joining such non-conjoined lumens, including small lumens typically requiring microsurgical technique.

30 Claims, 6 Drawing Sheets

U.S. PATENT DOCUMENTS

| | | | |
|---|---|---|---|
| 5,143,731 A | | 9/1992 | Viegas et al. |
| 5,180,392 A | * | 1/1993 | Skeie et al. ............... 623/23.64 |
| 5,183,879 A | | 2/1993 | Yuasa et al. |
| 5,366,735 A | | 11/1994 | Henry |
| 5,469,867 A | * | 11/1995 | Schmitt .................... 128/898 |
| 5,525,334 A | | 6/1996 | Ito et al. |
| 5,534,186 A | | 7/1996 | Walker et al. |
| 5,565,139 A | | 10/1996 | Walker et al. |
| 5,589,568 A | | 12/1996 | Higashijima et al. |
| 5,643,246 A | | 7/1997 | Leeb et al. |
| 5,651,979 A | | 7/1997 | Ron et al. |
| 5,653,744 A | | 8/1997 | Khouri |
| 5,681,576 A | | 10/1997 | Henry |
| 5,695,480 A | | 12/1997 | Evans et al. |
| 5,702,361 A | | 12/1997 | Evans et al. |
| 5,702,717 A | * | 12/1997 | Cha et al. ................... 424/425 |
| 5,726,456 A | | 3/1998 | Lupton et al. |
| 5,787,900 A | | 8/1998 | Butler et al. |
| 5,830,224 A | * | 11/1998 | Cohn et al. .................. 606/167 |
| 5,834,007 A | | 11/1998 | Kubota |
| 5,858,746 A | | 1/1999 | Hubbell et al. |
| 5,861,174 A | | 1/1999 | Stratton et al. |
| 6,004,573 A | | 12/1999 | Rathi et al. |
| 6,018,033 A | | 1/2000 | Chen et al. |
| 6,201,065 B1 | | 3/2001 | Pathak et al. |
| 6,309,663 B1 | | 10/2001 | Patel et al. |
| 6,413,537 B1 | | 7/2002 | Kwon et al. |
| 6,488,954 B1 | | 12/2002 | Yoon et al. |
| 6,562,362 B1 | | 5/2003 | Bae et al. |
| 6,660,247 B1 | | 12/2003 | Gutowska et al. |
| 6,743,436 B1 | | 6/2004 | Lee et al. |
| RE38,558 E | | 7/2004 | Emanuele et al. |
| 6,761,824 B2 | | 7/2004 | Reeve et al. |
| 6,761,903 B2 | | 7/2004 | Chen et al. |
| 6,897,064 B2 | | 5/2005 | Yoshioka et al. |
| 6,923,986 B2 | | 8/2005 | Pathak et al. |
| 6,939,364 B1 | | 9/2005 | Soltz et al. |
| 6,977,045 B2 | | 12/2005 | Reeve et al. |
| 6,991,804 B2 | | 1/2006 | Helmus et al. |
| 7,011,677 B2 | | 3/2006 | Wallace et al. |
| 7,018,645 B1 | | 3/2006 | Piao et al. |
| 7,033,571 B2 | | 4/2006 | Gutowska et al. |
| 7,044,982 B2 | | 5/2006 | Milbocker |
| 7,083,806 B2 | | 8/2006 | Rippon et al. |
| 7,160,931 B2 | | 1/2007 | Cheng et al. |
| 7,169,404 B2 | | 1/2007 | Hossainy et al. |
| 7,193,007 B2 | | 3/2007 | Cheng et al. |
| 7,641,643 B2 | | 1/2010 | Michael et al. |
| 7,691,140 B2 | | 4/2010 | Bates et al. |
| 2003/0191209 A1 | | 10/2003 | Guan et al. |
| 2004/0096508 A1 | | 5/2004 | Gutowska et al. |
| 2004/0213756 A1 | | 10/2004 | Michael et al. |
| 2004/0220283 A1 | | 11/2004 | Zhang et al. |
| 2004/0253277 A1 | | 12/2004 | Meadows et al. |
| 2004/0266983 A1 | | 12/2004 | Reeve et al. |
| 2005/0008610 A1 | | 1/2005 | Schwarz et al. |
| 2005/0027019 A1 | | 2/2005 | Zhang et al. |
| 2005/0079147 A1 | | 4/2005 | Delaey et al. |
| 2005/0143678 A1 | | 6/2005 | Schwarz et al. |
| 2005/0147585 A1 | | 7/2005 | Schwarz et al. |
| 2005/0181062 A1 | | 8/2005 | Appel et al. |
| 2005/0220881 A1 | | 10/2005 | Mehta et al. |
| 2006/0078616 A1 | | 4/2006 | Georgewill et al. |
| 2006/0269512 A1 | | 11/2006 | McDougal et al. |
| 2007/0202177 A1 | | 8/2007 | Hoang |
| 2007/0237740 A1 | | 10/2007 | Reddington et al. |
| 2008/0031847 A1 | | 2/2008 | Cohn |
| 2008/0045985 A1 | | 2/2008 | Gurtner et al. |
| 2008/0181952 A1 | | 7/2008 | Vogel et al. |
| 2008/0208163 A1 | | 8/2008 | Wilkie |
| 2008/0215036 A1 | | 9/2008 | Vogel et al. |
| 2008/0262519 A1 | | 10/2008 | Gurtner et al. |
| 2009/0162438 A1 | | 6/2009 | Fuller et al. |

FOREIGN PATENT DOCUMENTS

| | | |
|---|---|---|
| EP | 0 386 960 | 9/1990 |
| EP | 0 327 325 | 10/1996 |
| EP | 1 266 570 | 12/2002 |
| EP | 0 724 888 | 5/2003 |
| EP | 1 407 791 | 4/2004 |
| KR | 20040028336 | 4/2004 |
| WO | WO-96/33673 | 10/1996 |
| WO | WO 96/33673 | 10/1996 |
| WO | WO-02/14380 | 2/2002 |
| WO | WO-2004/084703 | 10/2004 |
| WO | WO-2005/037062 | 4/2005 |
| WO | WO-2005/046438 | 5/2005 |
| WO | WO-2005/100441 | 10/2005 |
| WO | WO-2006/119009 | 11/2006 |
| WO | WO 2007/149999 | 12/2007 |
| WO | WO-2008/018892 | 2/2008 |
| WO | WO-2008/033728 | 3/2008 |
| WO | WO 2008/073938 | 6/2008 |
| WO | WO-2008/103891 | 8/2008 |
| WO | WO 2009/086206 | 7/2009 |
| WO | WO 2009/086207 | 7/2009 |
| WO | PCT/US2010/023155 | 2/2010 |

OTHER PUBLICATIONS

U.S. Appl. No. 12/367,201, filed Feb. 6, 2009, C. Travis Rappleye et al.

Kamiji, T. et al., "Microvascular anastomosis using polyethylene glycol 4000 and fibrin glue," British Journal of Plastic Surgery, 1989, vol. 42, pp. 54-58.

Cong, Z et al., "Experimental Study on Microvascular Anastomosis Using a Dissolvable Stent Support in the Lumen", Microsurgery, 1991, vol. 12, pp. 67-71.

Kania, N. M. et al., "A new method of microvascular anastomosis: Clips with a soluble stent", 1998, pp. 245-248. (English abstract provided).

Moskovitz, M., "Microvascular Anastomoses Utilitzing New Intravascular Stents", 1994, vol. 32, pp. 612-618.

Nakata, S. et al., "End-to-side and end-to-end vascular anastomoses with a carbon dioxide laser", The Journal of Thoracic and Cardio-vascular Surgery, 1989, vol. 98, pp. 1-2.

Bavbek, T. et al., "Problems with Attempted Chorioretinal Venous anastomosis by Laswer for Nonischemic CRVO and BRVO", 2005, vol. 219, No. 5, pp. 1-2.

Beltran, S. et al., "Swelling Equilibria for Weakly Ionizable, Temperature-Sensitive Hydrogels", Macromolecules, 1991, vol. 24, No. 2, pp. 549-551.

Chen, G. et al., "Graft Copolymers That Exhibit Temperature-induced Phase Transitions Over a Wide Range of pH", Nature, 1995, vol. 373, pp. 49-52.

Dumortier et al., "A Review of Polexamer 407 Pharmaceutical and Pharmacological Characteristics" Pharmaceutical Research, 2006, vol. 23, No. 12, pp. 2709-2728.

Leung, P.C. et al., "Biodegradable, Thermosensitive Implant for Approximating Cylindrical Structures: A Preliminary Study", Microsurgery, 2003, vol. 23, pp. 123-129.

Park, T.G. et al., "Temperature Modulated Protein Release From pH/Temperature Sensitive Hydrogels" Biomaterials, 1999, vol. 20, pp. 517-521.

Park, T.G. et al., "Synthesis, Characterization, and Application of pH/Temperature-Sensitive Hydrogels", Proceed. Intern. Symp. Control. Rel. Bioact. Mater., 1990, vol. 17, pp. 112-113.

Steedman, H.F., "A New Ribboning Embedding Medium for Histology", Nature, 1957, vol. 179, pp. 1345.

Zhang, J. et al., "Synthesis and Characterization of pH-and Temperature-Sensitive Poly(Methacrylic acid)/Poly(N isopropylacrylamide) Interpenetrating Polymeric Networks" Macromolecules, 2000, vol. 33, pp. 102-107.

* cited by examiner

COMPOSITIONS AND METHODS FOR JOINING NON-CONJOINED LUMENS

CROSS-REFERENCE TO RELATED APPLICATIONS

This application is a continuation-in-part application of U.S. patent application Ser. No. 11/962,077, filed Dec. 20, 2007, which is a continuation-in-part application of U.S. patent application Ser. No. 11/766,779, filed Jun. 21, 2007, which claims the benefit under 35 U.S.C. §119(e) of provisional Patent Application Ser. Nos. 60/805,425, filed on Jun. 21, 2006, 60/806,242, filed on Jun. 29, 2006, and 60/914,635, filed on Apr. 27, 2007, all of which are incorporated herein by reference in their entirety.

FIELD OF THE INVENTION

This invention relates generally to compositions, methods, and kits for joining together non-conjoined lumens in a patient's body including vascular lumens. More particularly, in various aspects, this invention provides compositions, methods, and kits for joining such non-conjoined lumens, including small lumens typically requiring microsurgical techniques.

BACKGROUND OF THE INVENTION

Non-conjoined lumens arise in a variety of settings including surgical settings where the non-conjoined lumens are intentionally created or arise from lacerations or puncture wounds. Intentionally created non-conjoined lumens include those arising during surgical repair of e.g., treatment of a blockage in a lumen by bypass procedures, attaching a synthetic graft or during free tissue transfer in cosmetic surgical settings. Anastomosis is conducted to surgically reconnect the open ends of the lumen. Examples of anastomosis procedures include anastomotic procedures on the vasculature, the vas deferens, the fallopian tubes, the urinary tract, tear ducts, bowel, mammary glands, alimentary ducts, pancreatic ducts, bile ducts, etc. In each case, the anastomosis procedure creates a channel for the flow of a body fluid there through.

The anastomosis may be, for example, end-to-end, end-to-side, and side-to-side. As is apparent from their names, anastomosis may involve various configurations. For instance, one tubular tissue may be joined end-to-side with two tubular tissues, creating a three-channeled tubular tissue construct.

In the surgical context, end-to-end anastomosis, as is apparent from its name, is a surgical procedure for connecting an end or distal portion of one tubular tissue structure to an end or distal portion of another tubular tissue structure, such that a continuous lumen is created. (As used herein, "end" or "distal portion," refers to the open end of the tubular tissue.)

In an end-to-side anastomosis, a tubular tissue structure having a hole or open part is connected through the open part to an open or distal end of a tubular tissue to form a continuous lumen with a branched configuration. Similarly, in a side-to-side anastomosis, two non-conjoined lumens are merged together into a continuous lumen though a hole or opening on each of the lumens to be joined.

A successful anastomosis typically involves the smooth connection of lumens, such that the internal structure is not blocked and internal body fluid flow—such as blood, semen or food or gastrointestinal fluids—is restored or improved. Ideally, the matching up/ligation surgical procedure is rapid and precise, so that patient exposure while in a vulnerable state—such as having blood flow stopped—is minimized.

There are a variety of tubular tissues, and the lumen of the first tubular tissue may not be of the same diameter as the lumen of the second tubular tissue. Thus, because the delicate surgery may involve matching and ligating two (or more) non-identical tubular tissues, various ligation techniques have been used with varying rates of success. These include sutures, tissue adhesives, adhesive strips, and staples, clips and other devices. To some extent all of these materials involve the skill of the practitioner in anastomosis which is accurate, durable and free from conditions which could cause latent deleterious reactions in vivo.

The labor-intensive needle and thread remains the most-used technology as of the present day. Because of the complexity and judgment required in suturing, automated techniques are not well accepted. Calcified and diseased vessels provide mechanical challenges. Sutures may, in some instances, cause a reaction resulting in long term stenosis or fibrosis.

Other approaches to anastomosis include the use of sealants and bioglues for ligation. These may be used individually or in conjunction with suturing or other mechanical ligation techniques or devices. For example, one commercially available sealant CoSeal® (Angiotech Pharmaceuticals, Inc., Vancouver, B.C., Canada) may complement suturing in cardiovascular surgeries.

Mechanical anastomosis devices, such as clips, are also available. One commercially available device, the U-Clip™ (Medtronic, Minneapolis, Minn. 55432 USA), essentially provides a sharp, nitinol hook for knotting to compete anastomosis. The nitinol allows reversible deformation. The C-Port® (Cardica, Inc. Redwood City, Calif. 94063 USA) and related products are commercially available and use miniature stainless steel staples to securely attach the bypass graft to the coronary artery.

Before ligating end-to-end, for example, the practitioner must match up the lumens by the circumference of the vessel, using blood vessels as an illustration. Frequently, this is troublesome to the practitioner because the end of an tubular tissue—such as a clamped blood vessel devoid of blood—is not a perfectly round circle; rather it is in its unpressurized, deflated-looking state where a cross-sectional view of the circumference may be a circle, an oval or irregular, and, of course having no structural support from within, is unstably in any shape (unless the surrounding tissue possesses structural strength). The size of the vessels to be connected may also be different. Although blood vessels, for example, or other tubular tissues are somewhat elastic (deformable and returning to the original shape) or plastic (deforming, and not fully returning to the original shape), connecting the circumferences of the lumens such that upon ligation there is no or minimal leakage (in the vascular context, for example), requires a skilled practitioner.

In a microvascular context, anastomosis is performed between ends of blood vessels in the course of, for example, reattaching severed body parts or transplanting organs or tissues. Microvascular anastomosis is often performed by hand under a microscope, and is tedious and painstaking work. The blood vessels connected together often have different diameters, both of which are very small, on the order of about 1 to about 5 millimeters ("mm"). Although blood vessels are usually at least somewhat elastic, the practitioner must match up end to end (for example) two different shaped-different-sized circumferences and then stitch them together (for example). As a result, it can take many hours to complete just the microvascular anastomosis required to reconnect a severed body part or transplant an organ.

One attempt to provide a mechanism for performing such a microvascular anastomosis is the Microvascular Anastomotic Coupler System, available from Bio-Vascular, Inc. (San Diego, Calif., USA). In this mechanism, an end of each vessel to be connected is essentially turned outward ("everted") over a ring with a forceps or similar instrument. Each ring includes a number of pins over which the vessel is everted. The rings are then pressed together, such that the pins on each ring enter recesses in the other ring, connecting the rings and holding the ends of the vessels together. This system, however, is limited to use with two blood vessels having substantially the same diameter. Further, manual eversion of a blood vessel having a diameter on the order of one millimeter is difficult and painstaking, particularly when the eversion is to be substantially even around the circumference of the ring. Further, the rings provide a noncompliant anastomosis between the two vessels. Thus, although stabilizing the circumference facilitates the ability of the practitioner to match up vessels for end-to-end microvascular anastomosis, the device requires, essentially, practitioners skilled in microsurgical techniques.

For patients and practitioners, perhaps the most demanding anastomosis is incident to heart revascularization. The arteries that bring blood to the heart muscle (coronary arteries) can become clogged by plaque (a buildup of fat, cholesterol and other substances). This can slow or stop blood flow through the heart's blood vessels, leading to chest pain or a heart attack. Increasing blood flow to the heart muscle can relieve chest pain and reduce the risk of heart attack. A patient may undergo one, two, three or more bypass grafts, depending on how many coronary arteries are blocked.

Coronary artery bypass graft surgery ("CABG", sometimes pronounced "cabbage" by practitioners) reroutes, or "bypasses," blood around clogged arteries to improve blood flow and oxygen to the heart. In performing the CABG anastomosis, a segment of a healthy blood vessel from another part of the body is used to make a detour around the blocked part of the coronary artery. This healthy blood vessel may be, for example, an artery present in the thoracic cavity, or may be a piece of a long vein from the patient's leg. In some circumstances, grafts from non-autologous sources may be used, such as synthetic tubular tissues or animal tubular tissues. Regardless of the source of the healthy blood vessel, one end is connected to the large artery leaving the patient's heart (the aorta), and the other end is attached or "grafted" to the coronary artery below the blocked area. In this way of "rewiring" the vasculature, substantially unobstructed blood flow to the heart muscle is resumed.

Conventionally, a pump oxygenator (heart-lung machine) is used for coronary bypass graft operations. Medicines are used to stop the patient's heart, which allows the practitioner to operate without the heart beating. The heart-lung machine keeps oxygen-rich blood moving throughout the patient's body. For this conventional heart bypass graft surgery, a team of practitioners is needed (a surgeon, cardiac anesthesiologist and surgical nurse, and a perfusionist (blood flow specialist)). Multiple practitioners, additional complexity, and, as a practical matter, additional health care cost is involved over surgical procedures involving fewer practitioners and procedures.

Moreover, blood quality may be degraded as the heart-lung machine repetitively pumps the patient's blood through the systemic circulation. The blood may embolize or clot in the distal circulation, or form clots which migrate to the distal vasculature, and cause a stroke.

"OffPump" coronary artery bypass grafting, also called beating heart bypass grafting, takes place while the heart continues to beat, but a mechanical device may be used in an attempt to steady the surrounding vasculature, so that the practitioner can perform the graft. Off pump coronary artery bypass surgery may reduce this risk. Frequently, because the graft must be performed on arteries in locations directly affected by the beating heart, stabilizing mechanisms are not thoroughly effective, and the practitioner must suture the graft while the graft is moving in conjunction with the heart beat, at least to some extent. Thus, the graft quality may be compromised.

Although, in a bypass surgery time is of the essence, the practitioner cannot rush through without thoroughly and precisely anastomising the graft(s). In conventional coronary artery bypass surgery, three critical determinates that affect the outcome of a bypass surgery are:

(1) time the patient spends on cardiopulmonary bypass,
(2) time the patient spends with a clamped aorta, and
(3) the quality of the anastomosis.

After an hour, the risk of patient morbidity is thought to increase perhaps due to the heart-lung machine degrading the quality of the blood as it is circulated through the systemic circulation. Bypass surgeries, however, often last three hours or longer. Moreover, where the aorta is clamped and blood therefore cannot pass through, the blocked blood is thought to cause additional issues.

Anastomosis is time-consuming. The average time for suturing one anastomosis is approximately fifteen to sixty minutes. An average CABG procedure is thought to involve approximately five anastomoses. Therefore, the average time for graft suturing exceeds the sixty-minute threshold for increased patient morbidity. Patients treated with conventional coronary surgery and placed on cardiopulmonary bypass would benefit from reducing the amount of time spent performing each anastomosis.

In "off pump" procedures where the heart remains beating, the difficulty of suturing an anastomosis graft on a moving surface of the heart may degrade the quality of such grafts completed on patients. An anastomosis differs from straight line suturing in that each suture has a different orientation that is based on its position around the cross-sectional circumference of the blood vessel graft. It can be appreciated that some of the sutures are easily made from on top of the conduit or blood vessel graft, while others are more difficult to complete as they are beneath the conduit. It can be further appreciated that performing such complex suturing procedures on a moving platform, such as the beating heart, further increases the difficulty associated with such suturing procedures. Improperly connecting blood vessel grafts to the patient may present substantial post-operative complications and/or increase operating room time spent correcting the improperly connected graft.

Accordingly, for surgical anastomosis, both practitioners and patients would benefit from faster procedures allowing patients to minimize procedure time, and simpler methods allowing reduced complexity and ease of use and higher quality anastomosis with fewer complications.

SUMMARY OF THE INVENTION

This invention is directed to the discovery that the stabilization of the geometry of the terminal portions of tubular tissues facilitates joining such non-conjoined tissues. In one aspect, such stabilization is achieved by use of biocompatible solid materials which can be placed into the terminal portions of at least one of the lumens of the tubular tissues to be joined.

Thus, in one aspect, this invention relates to a method for joining at least two non-conjoined lumens in a patient which method comprises:
  a) providing a biocompatible solid mass in at least the distal portion of at least one of the lumens;
  b) aligning the lumens;
  c) joining the aligned lumens to form a conduit; and
  d) removing the biocompatible solid mass thereby establishing flow through the conduit.

In one embodiment, the biocompatible solid mass is placed in the distal portion (opening) of each lumen to be joined. In another embodiment, the solid mass is placed in the distal portion of a first lumen in a manner in which the solid mass protrudes from the distal portion such that this protrusion can be used as a male mating functionality with the distal portion of the second lumen which acts as a female mating functionality.

The biocompatible solid mass employed in the methods described herein is not critical provided that it imparts sufficient structural integrity to the distal portion of the lumen. Examples of suitable solid masses include sol-gel solutions, waxes, thixotropic agents, etc.

The joining of the lumens may be accomplished by applying a biocompatible adhesive, suturing, or applying laser, such as laser welding or laser soldering.

The removal of the solid mass can be accomplished using any of a number of physical properties of the mass such as melting, phase change, change in viscosity, dissolution in the body fluid and/or combinations of these properties.

Accordingly, in another of its method aspects, there is provided a method for joining at least two non-conjoined lumens having distal (open) ends, comprising the steps of:
  providing a phase-reversible sol-gel inside at least a portion of the distal end of the first lumen in a manner which imparts structural integrity to said portion of the first lumen;
  providing a phase-reversible sol-gel inside at least a portion of the distal end of a second lumen in a manner which imparts structural integrity to said portion of the second lumen;
  aligning the distal portions of the first and second lumens;
  joining said lumens so as to provide for a conduit;
  inducing a phase change in the phase-reversible sol-gel in said conduit wherein said sol-gel phase changes to a liquid phase; and
  allowing flow through said conduit.

In still another of its method aspects, there is provided a method for joining at least two non-conjoined lumens having distal (open) ends, comprising the steps of:
  providing a phase-reversible sol-gel inside at least a portion of the distal end of a first lumen in a manner which imparts structural integrity to said portion of the first lumen wherein said sol-gel protrudes from the distal end;
  mating the distal end of a second lumen with said protrusion from the first lumen thereby aligning the first and second lumens;
  joining said lumens so as to provide for a conduit;
  inducing a phase change in the phase-reversible sol-gel in said conduit wherein said sol-gel phase changes to a liquid phase;
  allowing flow through said conduit.

In another of its method aspects, there is provided a method for joining at least two non-conjoined lumens in a patient which method comprises:
  (a) providing a biocompatible phase-reversible sol-gel composition in at least the distal portion of at least one of the lumens in a manner which imparts structural integrity to said portion of the lumen or lumens;
  (b) aligning the lumens;
  (c) closing the aligned lumens to form a conduit; and
  (d) removing the sol-gel composition thereby establishing flow through the conduit;
  wherein the phase-transition of the sol-gel composition is triggered by a stimulus selected from a change in temperature, a change in pH, a change in ionic strength, a change in pressure, a change in electric field, a change in magnetic field, a change in electron magnetic radiation, a change in light or ultraviolet light, a change in concentration, a change in osmolarity, and combinations thereof.

In some embodiments using a sol-gel composition, the step of providing the sol-gel composition in the lumen comprises:
  placing the phase-reversible sol-gel in a gel phase inside at least a portion of the distal end of at least one of the lumens in a manner which imparts structural integrity to said portion of the lumen.

In some embodiments using a sol-gel composition, the step of providing the sol-gel composition in the lumen comprises:
  placing the phase-reversible sol-gel in a liquid phase inside at least a portion of the distal end of at least one of the lumens; and
  inducing a phase transition change in the phase-reversible sol-gel in the lumen wherein the liquid phase changes to a gel phase which imparts structural integrity to said portion of the lumen.

In some embodiments, the method further comprises a step before the step of providing the sol-gel composition in the lumen, which step comprises arresting the flow of body fluid in the lumens. In some embodiment, the arresting of the flow of body fluid through the lumen, for example a blood vessel, comprises applying a clamp on the lumen, or by conventional means such as applying external pressure, e.g., pressing down with a finger or tourniquet, on the vasculature, or providing a vessel loop or vessel tie upstream from the point of severance or on both sides of the point of severance, so that the flow of body fluid in the lumen, such as blood, is reduced or stopped.

In another of its method aspects, there is provided a method for joining at least two non-conjoined lumens having distal (open) ends, comprising the steps of:
  providing a solid biocompatible wax inside at least a portion of the distal end of the first lumen in a manner which imparts structural integrity to said portion of the first lumen;
  providing a solid biocompatible wax inside at least a portion of the distal end of a second lumen in a manner which imparts structural integrity to said portion of the second lumen;
  aligning the distal portions of the first and second lumens;
  joining said lumens so as to provide for a conduit; and
  converting the wax from a solid to a dissolved and/or liquid form such that flow is established through said conduit.

In still another of its method aspects, there is provided a method for joining at least two non-conjoined lumens having distal (open) ends, comprising the steps of:
  providing a solid biocompatible wax inside at least a portion of the distal end of a first lumen in a manner which imparts structural integrity to said portion of the first lumen which wax protrudes from said distal end;
  mating the distal end of a second lumen with said protrusion from the first lumen thereby aligning the first and second lumens;
  joining said lumens so as to provide for a conduit; and converting the wax from a solid to a dissolved and/or liquid form such that flow is established through said conduit.

In another of its method aspects, there is provided a method for joining at least two non-conjoined lumens having distal (open) ends, comprising the steps of:
  providing a solid biocompatible thixotropic agent inside at least a portion of the distal end of the first lumen in a manner which imparts structural integrity to said portion of the first lumen;
  providing a solid biocompatible thixotropic agent inside at least a portion of the distal end of a second lumen in a manner which imparts structural integrity to said portion of the second lumen;
  aligning the distal portions of the first and second lumens;
  joining said lumens so as to provide for a conduit; and
  converting said thixotropic agent from a solid to a dissolved and/or liquid form such that flow is established through said conduit.

In still another of its method aspects, there is provided a method for joining at least two non-conjoined lumens having distal (open) ends, comprising the steps of:
  providing a solid biocompatible thixotropic agent inside at least a portion of the distal end of a first lumen in a manner which imparts structural integrity to said portion of the first lumen which agent protrudes from said distal end;
  mating the distal end of a second lumen with said protrusion from the first lumen thereby aligning the first and second lumens;
  joining said lumens so as to provide for a conduit; and
  converting said thixotropic agent from a solid to a dissolved and/or liquid form such that flow is established through said conduit.

In still another of its method aspects, there is provided a method of connecting ducts within a living mammal, comprising the steps of:
  providing a phase-reversible gel inside a first hollow duct in a manner which holds the first duct open;
  providing a phase-reversible gel inside a second hollow duct in a manner which holds the second duct open;
  applying adhesive between an end of the first duct and an end of the second duct and allowing the adhesive to form bonds between the first and second ducts;
  inducing a phase change in the phase-reversible gel inside the first duct and inside the second duct; and
  allowing flow through the first duct to the second duct.

In some embodiments, the adhesive is further placed on the out surface of both ducts to join them together.

In still another embodiment, this invention provides a method for joining at least two non-conjoined lumens in a patient, wherein at least one of the lumens has at least one clamp to arrest the flow of the fluid therein, which method comprises:
  (a) providing a biocompatible solid mass in at least the distal portion of at least one of the lumens;
  (b) aligning the lumens;
  (c) closing the aligned lumens to form a conduit;
  (d) inducing a phase transition of the solid mass wherein the solid mass changes from a solid phase to a liquid phase;
  (e) confirming substantial completion of the phase transition; and
  (f) removing the clamp(s) thereby establishing flow through the conduit.

In some embodiments, the method further comprises a step of approximating the lumens in a connecting position prior to the step of providing the biocompatible solid mass in the lumen(s). In some embodiments the approximating the lumens comprises partially suturing the lumens.

In some embodiments, all non-conjoined lumens have clamps.

In some embodiments, the method further comprises flushing the distal portion of the clamped lumen with a biocompatible liquid prior to the step of providing the biocompatible solid mass in the lumen.

In some embodiments, the method is a method for joining at least two non-conjoined lumens in a patient, wherein at least one of the lumens has a clamp to arrest the flow of the fluid therein, which method comprises:
  (a) providing a biocompatible phase-reversible sol-gel composition in a gel phase in at least the distal portion of at least one of the lumens;
  (b) aligning the lumens;
  (c) closing the aligned lumens to form a conduit;
  (d) inducing a phase transition of the sol-gel wherein the sol-gel changes from the gel phase to a liquid phase;
  (e) confirming substantial completion of the phase transition; and
  (f) removing the clamp(s) thereby establishing flow through the conduit.

In some embodiments, the method is a method for joining at least two non-conjoined lumens in a patient, which method comprises:
  (a) approximating the lumens in a connecting position;
  (b) providing a biocompatible solid mass in the distal portion of both lumens;
  (c) closing the lumens to form a conduit;
  (d) inducing a phase transition of the solid mass wherein the solid mass changes from a solid phase to a liquid phase; and
  (e) establishing flow through the conduit.

In some embodiments, the method is a method for joining at least two non-conjoined lumens in a patient, which method comprises:
  (a) approximating the lumens in a connecting position;
  (b) providing a biocompatible phase-reversible sol-gel composition a gel phase in the distal portion of both lumens;
  (c) closing the lumens to form a conduit;
  (d) inducing a phase transition of the sol-gel wherein the sol-gel changes from the gel phase to a liquid phase; and
  (e) establishing flow through the conduit.

In some embodiments of the above method, step (e) comprises (e1) and (e2), wherein (e1) comprises confirming substantial completion of the phase transition, and wherein (e2) comprises removing the clamps thereby establishing flow through the conduit and removing the sol-gel composition.

In some embodiments, the approximating the lumens in a connecting position comprises partially suturing the lumens.

In some embodiments, the above method further comprises a step before the step of providing the sol-gel composition in the lumen, which step comprises arresting the flow of body fluid in the lumens.

In some embodiments, the arresting the flow of body fluid in the lumen comprises clamping at least one of the lumens. In some embodiments, the arresting the flow of body fluid in the lumen comprises clamping all the lumens to be joined.

In some embodiments, the arresting the flow of body fluid in the lumen comprises applying a pressure on at least one of the lumens.

In some embodiments, the method further comprises flushing the distal potion of the clamped lumen with a biocompatible liquid prior to the step of providing the sol-gel composition in the lumen.

In some embodiments, the invention provides a method for joining at least two non-conjoined lumens in a patient, wherein at least one of the lumens has a clamp to arrest the flow of the fluid therein, which method comprises:

- flushing the distal potion of the clamped lumen with a biocompatible liquid;
- approximating the lumens in a connecting position, which approximating comprises partially suturing the lumens;
- providing a biocompatible phase-reversible sol-gel composition in a gel phase in the distal portion of both lumens;
- closing the lumens to form a conduit with a biocompatible adhesive;
- inducing a phase transition of the sol-gel wherein the sol-gel changes from the gel phase to a liquid phase;
- confirming substantial completion of the phase transition; and
- removing the clamps thereby establishing flow through the conduit and removing the sol-gel composition.

In another aspect, this invention provides methods for imaging the joinder (ligation) of at least two non-conjoined lumens using the methods of this invention and the visualization of the geometry of the distal portions of the lumens in a patient.

In some embodiments, the method is a method for imaging the joinder (ligation) of at least two non-conjoined lumens and the stabilization of the geometry of the distal portion of the lumens in a patient, the method comprises:

(a) acquiring an image of a biocompatible solid mass in at least the distal portion of at least one of the lumens;
(b) acquiring an image showing alignment of the lumens and closure of the aligned lumens to form a conduit.

In some embodiments, the method is a method for imaging the joinder (ligation) of at least two non-conjoined lumens and the stabilization of the geometry of the distal portion of the lumens in a patient, wherein at least one of the lumens is clamped to arrest the blood flow, the method comprises (a) acquiring an image of a biocompatible solid mass convertible by phase change to a flowable liquid in at least the distal portion of at least one of the lumens in proper position to impart structural integrity for the non-conjoined lumens;
(b) acquiring an image of the proper alignment of the lumens to be joined;
(c) acquiring an image of the closing of the lumens; and
(d) acquiring an image of the removal of the clamps.

In some embodiments, the method further comprises acquiring an image of the internal walls of the distal portion of the lumen before and/or after the lumen is flushed with a biocompatible liquid.

In some embodiments, the method is a method for imaging the joining of at least two non-conjoined lumens and the stabilization of the geometry of the distal portions of the lumens in a patient, the method comprises (a) acquiring an image of the approximation of the lumens for a connecting position;
(b) acquiring an image of a solid-mass convertible by phase change to a flowable liquid in the distal portion of both lumens in proper position for joining the non-conjoined lumens; and
(c) acquiring an image of the closure of the lumens to form a conduit.

The solid mass includes any of those described herein.

In some embodiments, the method is a method for imaging the joining at least two non-conjoined lumens and the stabilization of the geometry of the distal portions of the lumens in a patient, wherein at least one of the lumens is clamped, the method comprises (a) acquiring an image of the internal walls of the distal portion of the lumen after the lumen is flushed with a biocompatible liquid;
(b) acquiring an image of the approximation of the lumens for a connecting position;
(c) acquiring an image of a biocompatible phase-reversible sol-gel composition in a gel phase in the distal portion of both lumens in proper position for joining the non-conjoined lumens;
(d) acquiring an image of the closure of the lumens to form a conduit; and
(e) acquiring an image of the removal of the clamps and establishment of the flow of the body fluid.

In another aspect, this invention provides methods for visualizing guidance for the methods of this invention for joining at least two non-conjoined lumens in a patient.

In some embodiments, the method is a method for visualizing guidance for joining at least two non-conjoined lumens and the stabilization of the geometry of the distal portions of the lumens in a patient, the method comprises (a) displaying the provision of a biocompatible solid mass convertible by phase change to a flowable liquid in at least the distal portion of at least one of the lumens in proper position to impart structural support for the non-conjoined lumens;
(b) visualizing the proper alignment of the lumens to be joined;
(c) visualizing the closing of the lumens form a conduit; and
(d) visualizing the induction of the phase change of the biocompatible solid mass in the lumen where the solid mass changes from a solid state to a flowable liquid state.

In some embodiments, the method is a method for visualizing guidance for joining at least two non-conjoined lumens and the stabilization of the geometry of the terminal portions of the lumens in a patient, wherein at least one of the lumens has a clamp, the method comprises (a) displaying the provision of a biocompatible solid mass convertible by phase change to a flowable liquid in at least the distal portion of at least one of the lumens in proper position to impart structural support for the non-conjoined lumens;
(b) visualizing the proper alignment of the lumens to be joined;
(c) visualizing the closing of the lumens to form a conduit; and
(d) visualizing the removal of the clamps.

A method for visualizing guidance for joining at least two non-conjoined lumens and the stabilization of the geometry of the terminal portions of the lumens in a patient, the method comprises (a) visualizing the approximation of the lumens for a connecting position;
(b) displaying the provision of a biocompatible phase-reversible sol-gel composition in a gel phase in the distal portion of both lumens in proper position for joining the non-conjoined lumens; and
(c) monitoring closure of the lumens to form a conduit.

In some embodiments, the method further comprises visualizing the internal walls of the distal portion of the lumen before and/or after the lumen is flushed with a biocompatible liquid.

In some embodiments, the method further comprises monitoring the flow of body fluid through the conduit.

A method for visualizing guidance for joining at least two non-conjoined lumens and the stabilization of the geometry of the terminal portions of the lumens in a patient, wherein at least one of the lumens has a clamp, the method comprises (a) visualizing the internal walls of the distal portion of the lumen after the lumen is flushed with a biocompatible liquid;
(b) visualizing the approximation of the lumens for a connecting position;
(c) displaying the provision of a biocompatible phase-reversible sol-gel composition in a gel phase in the distal portion of both lumens in proper position for joining the non-conjoined lumens;
(d) monitoring by visualization closure of the lumens to form a conduit; and
(f) monitoring the flow of body fluid through the conduit.

In another aspect, this invention provides a method for evaluating the effectiveness of the methods of this invention for joining non-conjoined lumens in a patient.

In some embodiments, the method is a method for evaluating the effectiveness of surgical joining of at least two non-conjoined lumens in a patient using a thermoreversible sol-gel, the surgical joining procedure comprising a clamp on at least on one of the lumens to arrest the flow of the fluid therein and the thermoreversible gel in at least the distal portion of at least one of the lumens, alignment of the lumens, closure of the aligned lumens to form a conduit, induction of a phase change of the gel to a flowable liquid, substantial completion of the phase change and removal of the clamp, the evaluation method comprising (a) measuring the serum concentration of biomarkers indicative of myocardial performance or the performance of other organs connected to the conjoined lumens;
and/or
(b) measuring the diameters of the conjoined lumens, for example using CT angiography;
and/or
(c) determining patency and flow, for example through ultrasonic Doppler imaging;
and/or
(d) monitoring the presence of the flowable liquid in the serum or urine.

This invention is also directed to novel compositions useful in the methods described above. For example, in one embodiment, this invention is directed to thermoreversible compositions having a transition temperature of between 0° C. and 45° C.

In one embodiment, the thermoreversible sol-gel comprises:
a) a biocompatible polymer and
b) water;
wherein the thermoreversible so-gel has a sol-gel transition temperature of from about 35° C. to 42° C. and a modulus of from at least about 100 to about 500,000 Pascals.

In another embodiment, the thermoreversible sol-gel has a sol-gel transition temperature of between 15° C. and 35° C. and a modulus of from at least about 100 to about 500,000 Pascals.

In another embodiment, the thermoreversible sol-gel has a modulus of from at least about 8,000 Pascals.

In one embodiment, the polymer is a block co-polymer of polyoxyethylene and polyoxypropylene or mixtures of such block copolymers. In another embodiment, the composition is sterile.

In another embodiment, the sol-gel composition that is a gel or solid at a temperature below the transition temperature and a liquid above the transition temperature.

In another aspect, the thermoreversible sol-gel further comprises a biocompatible protein which increases the phase transition temperature of the composition while the structural integrity of the sol-gel modulus in the gel state.

In still another embodiment, the solid mass may contain a biocompatible dye so as to facilitate the alignment of the first and second lumen.

This invention is also directed to novel kits useful in the methods described above. In one embodiment, the kit comprises a delivering device; and a composition selected from a sol-gel, a wax, and a thixotropic material. In another embodiment, the kit further comprises at least one clamp for closing at least one of the non-conjoined lumen. In still another embodiment, the kit further comprises a biocompatible adhesive for sealing the lumens.

The present invention also includes use of any of the materials or methods as disclosed herein for manufacture of a medicament for joining lumens, particularly in a live patient, as further described herein. Thus, in one embodiment, the present invention provides a biocompatible solid mass for use in joining at least two non-conjoined lumens in a patient in a method which comprises:

a) placing the a biocompatible solid mass in at least the distal portion of at least one of the lumens;
b) aligning the lumens;
c) closing the aligned lumens to form a conduit; and
d) removing the solid mass thereby establishing flow through the conduit.

In another aspect, the invention is directed to a vessel of a cardiovascular system of a mammal, wherein the vessel has a phase-reversible sol-gel composition positioned in the vessel in a manner and in an amount sufficient to hold walls of the vessel open in a fashion similar to when blood flows through the vessel, wherein the phase-transition of the sol-gel composition is triggered by an environment condition selected from a change in temperature, a change in pH, a change in ionic strength, a change in pressure, a change in electric field and combinations thereof.

The methods, compositions and kits of this invention may be used in both human and non-human mammals.

These and other embodiments of the invention are further described in the text that follows.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
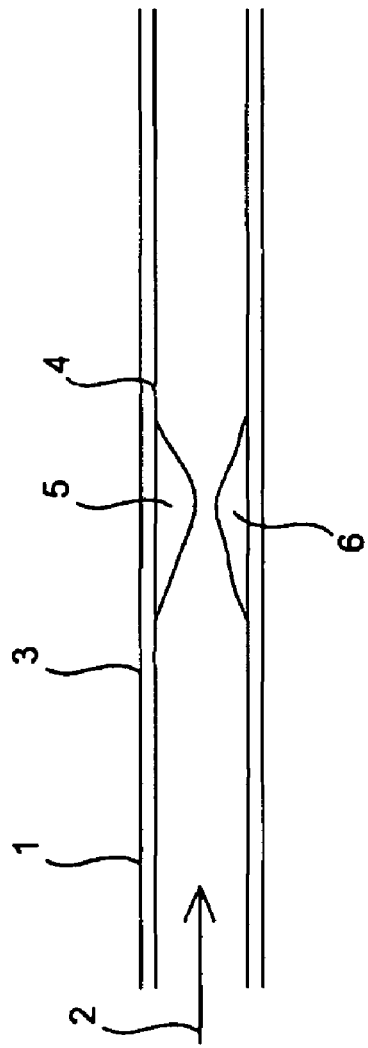
FIG. 1 is a schematic cross-sectional view of a tubular tissue with a partial blockage.

Before the present compositions, medical systems, kits, and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a thermoreversible gel" includes a plurality of such gels and reference to "the adhesive" includes reference to one or more adhesives and equivalents thereof known to those skilled in the art, and so forth.

I. DEFINITIONS

Unless defined otherwise, all technical and scientific terms used herein have the same meaning as commonly understood by one of ordinary skill in the art to which this invention belongs. As used herein the following terms have the following meanings. If not defined, a term has its art recognized meaning.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., pH, temperature, amount, concentration, including range, indicates approximations which may vary by (+) or (−) 10%, 5%, 1% or 0.1%.

The term "patient" refers to mammals and includes humans and non-human mammals.

The term "surgical" relates to any medical procedure where the inner organ or issue of a patient is accessed to investigate and/or treat a pathological condition such as disease or injury, to help improve or alter bodily function or appearance, or for other reasons. As used herein, "surgical" relates to procedures of accessing a patient's inner organ or tissue via an incision or an opening on the patient and via needle-puncture of the skin, such as in percutaneous approaches and other minimally invasive procedures, such as laparoscopic surgeries.

The term "lumen" refers to the hollow tube and the surrounding tissue defining the hollow tube, such as a blood vessel, a vas deferens, a fallopian tube, urinary tract, a tear duct, bowel, a mammary gland, an alimentary duct, a pancreatic duct, a bile duct, and the like. A lumen also includes artificial ducts, such as ePTFE grafts. The term "lumen" is used interchangeably with the term "duct."

The term "conduit" refers to the hollow tube formed by the joined lumens which can accommodate flow of a body fluid after removal of the solid mass placed therein or clamps placed thereon.

The term "biocompatible" as used with terms such as "biocompatible polymer", "biocompatible compound" and the like, refer to materials which, in the amounts employed, are non-toxic and substantially non-immunogenic when used internally in a subject such as a human patient.

The term "biocompatible solid mass" refers to a biocompatible mass having sufficient structural rigidity to maintain the shape of the filled lumen (i.e. impart structure integrity) during joining of the distal opening of the lumens and which solid mass can be subsequently removed from the joined lumens so as to permit flow there through. Examples of biocompatible solid masses include sol-gel compositions, waxes, thixotropic agents, and the like. In a preferred embodiment, the solid mass has a modulus of from about 100 to 500,000 Pascals or a yield stress of about 100 to 500,000 Pascals for the thixotropic solid mass. More preferably, the solid mass has a modulus or a yield stress of from about 8,000 to 50,000 or 10,000 to 50,000 Pascals and, still more preferably, from about 12,000 to 40,000 Pascals.

The term "providing" as used in, for example, "providing a solid mass in a distal end of a lumen" and the like, refers to the act of causing a solid mass to be present in the lumen to support the structural integrity of the lumen. The act can be "placing", "delivering" or the like, the solid mass can be placed in the lumen in a solid state or in a liquid state and being transferred into a solid state while inside the lumen.

The term "non-conjoined lumen" refers to a lumen having an open end or a hole where a body fluid that the lumen carries or should carry will undesirably leak out if the open end or hole is not occluded or connected to another lumen to form a continuous lumen in which the body fluid can circulate or be delivered to the desired destination without undesired leakage.

The term "distal end" and "opening" of a lumen are used interchangeably herein and refer to the opening of the lumen, for example, the two ends created when a lumen is surgically divided into two parts. "Distal end" or "opening" also refers to a hole cut on part of the wall of a lumen although the lumen is not completely divided, as in the case of an end-to-side or side-to-side anastomosis.

The term "distal portion of the lumen" refers to the portion of the lumen adjacent to the opening in the lumen. Thus, for example, when a lumen is surgically cut, the resulting two openings define the distal portion of what are now first and second lumens. Distal portion of the lumen also refers to the portion adjacent to the hole of a lumen to be used in an end-to-side or side-to-side anastomosis procedure. In surgical procedures where a clamp is employed on each of the non-conjoined lumens, the distal portion is the portion from the clamp to the end of the open lumen.

The term "joining" refers to any method wherein the first and second lumens are structurally joined together including by way of example, suturing, use of biocompatible glues, etc. In a preferred embodiment, joining of the lumens is conducted under conditions where there is little or no leakage of body fluid from the juncture of the joined lumens.

The term "aligning" refers to the act of bringing the lumens to be joined in a position that the lumens may be connect in a desirable manner, which may include matching up the ends of the lumens and pushing the matched ends of the lumens in contact of each other. Preferably, aligning is done without causing substantial tension to the lumens and to the respective tubular tissues they connect to.

The term "approximating" refers to the act of bringing the lumens to a position or to a close proximity of a position that they are to be connected. When two lumens are approximated, they are close to each other but there may be gaps between the ends of the lumens so that a solid mass can be applied to the inside of the lumens to provide structural support.

The term "substantial completion" as used in, for example, "confirming substantial completion of phase change," refers to the amount of the phase change that would ensure that the sol-gel composition can be safely removed from the lumen by the flow of body fluid in the lumen without causing undesirable blockage in the lumen, for example in a portion of a blood vessel connected to and is smaller than the vessel being joined. In some embodiments, "substantial completion" refers to equal to or greater than about 50%, 80%, 90%, or 95% and up to 100% phase change.

The term "removing the solid mass" refers to any of a number of physiological or chemical means or combinations thereof to remove the solid mass from the conduit formed by the joined lumens. For example, the solid mass may be removed by melting as in the case of waxes having a melting point at or slightly above body temperature followed by flushing with the body fluid inside the lumen. Alternatively, the solid mass may be soluble in the body fluid when flow is restored in the joined lumens. Still further, a combination of melting and dissolution can be used. Thixotropic agents will significantly reduce their viscosity in the presence of shear forces and become fluid in nature. As such, in this case, removing the solid mass of a thixotropic agent can involve either internally applied shear such as that arising from restoring flow or externally applied shear. Sol-gel compositions undergo a phase transfer from a solid to a liquid under defined phase transfer triggers such as temperature, pH or other ion concentration, light, ultrasound, pressure, etc. In such cases, conventional triggers are employed to effect phase transfer from a solid to a liquid. The solid mass may dissolve in the body fluid. Such liquids will be engrained in the body fluid and become part of the systemic flow of that fluid until removed by the body.

The term "sol-gel" refers to a composition, typically polymeric, which, upon a defined trigger, undergoes a phase transition from a flowable composition with a viscosity of less than 2000 Pascal-seconds ("liquid") to a gel or relatively solid form with a viscosity of greater than 10,000 Pascal-seconds ("gel" or "solid") which transition is preferably but not necessarily reversible. As is well known in the science of rheology, complex viscosities of compositions are reported in Pascal-seconds and all viscosities reported in this application are reported as complex viscosities. When reversible, the composition is referred to as a "phase-reversible sol-gel". Preferably reversing phase from a solid to a liquid occurs in less than 5 minutes, more preferably in less than 2 minutes and even more preferably in less than 1 minute.

The term "trigger" or "stimulus" refers to the environmental condition that triggers the phase transition from sol to gel or vice versa. Such triggers may include a change in temperature, a change in pH, a change in ionic strength, a change in pressure, a change in electric field, a change in magnetic field, a change in electron magnetic radiation, a change in light or ultraviolet light, a change in concentration, a change in osmolarity, and combinations thereof. One embodiment of this invention comprises an aqueous-based solution or compound having low viscosity at physiological conditions, but exhibiting rapid gelation at conditions slightly outside of (e.g., ±2% to ±10%) physiological conditions. In the case of temperature as a stimulus, the transition from a liquid state to gelled state may occur at temperatures that are slightly outside (e.g., ±2% to ±10%) physiological temperatures. Such temperatures are referred to as "near" the normal physiological body temperature. The flowable liquid solution gels in response to one or multiple in-situ environmental stimuli, and may be reversible. The composition should have biocompatibility with the host tissue. The invention is preferably carried out with a composition which is comprised only of biocompatible materials and more preferably materials approved by regulatory agencies "Thermoreversible sol-gel" refers to a composition that undergoes a phase transition from a liquid flowable material to a solid or gel like material when the temperature is raised to or above a transition temperature, and undergoes a phase transition from a solid or gel like material to a liquid flowable material when the temperature is lowered to or below the transition temperature. Such phase-transition is reversible.

Although the working example herein is a thermoreversible sol-gel composition, using temperature to initiate phase-transition, other sol-gel compositions systems may be similarly used, and may be selected with regard to the particular anastomosis use. For example, the phase change may be due to other stimuli such as pH, ion concentration (e.g., a change in calcium ion concentration or ionic strength), light, pressure, ultrasound, electric field, magnetic field, electronmagnetic radiation, osmolarity, solvent composition, a change in the concentration of the composition, and a combination thereof.

The sol-gel compositions may be deployed in either a substantially solid or substantially liquid state. Although the terms "substantially solid" and "substantially liquid" are relative with respect to each other, in the context of anastomoses where the utility lies, in part, in structural support for the geometry of the terminus of a tubular tissue, "substantially solid" is used herein to mean that the sol-gel is sufficiently stiff to provide such structural support; "substantially liquid" is used herein to mean that the sol-gel is insufficiently solid to provide such structural support.

For example, where tubular tissue is very narrow, a practitioner may wish to deploy the sol-gel via injection, as presented in further detail herein.

The term "arresting" the flow of a body fluid refers the act of stopping, substantially stopping, or reducing the flow of the body fluid. This can be done a number of ways, such as by using a clamp, providing a vessel loop, silk tie, applying a direct pressure (for example, using a finger or tournequette).

The term "clamp" refers to conventional mechanical devices suitable for application to a lumen to arrest the flow of body fluid therein, for example, stopping or reducing the flow of blood in a vessel, where the devices can be retrieved after they are no longer needed, thereby restoring flow. Clamps include any surgical clamps suitable for clamping the vessels to be operated on from the outside, such as clamps, clips and tourniquets or snares. Clamps also include devices that are applied to the inside of a lumen, such as a balloon catheter that is placed inside a blood vessel and inflated to stop blood flow. Suitable clamps are known in the art.

The terms "adhesive", "surgical adhesive", "glue", "biocompatible glue" or "sealant" and the like are used interchangeably herein. These terms are used to describe compounds which are or can be used in binding one tissue to another tissue. The glue may operate by the formation of covalent bonds and allow the tissues to contact each other and naturally heal or grow together. The adhesive may be comprised of a cyanoacrylate-based adhesive, a fibrin-based adhesive, a polyurethane-based adhesive, a polyisocyanate-based adhesive, a polyethylene glycol-based glue, a latex glue, a biologics glue (also known as a protein-based glue, such as those comprising serum albumin (such as human, bovine, or porcine serum albumin), and glutaraldehyde), or an ultraviolet curable glue. The adhesives may include any biocompatible material which when added to the adhesive, produces an open cell geometry upon curing in situ to promote tissue ingrowth. For example, such material can include a foaming agent or porogen, such as sodium chloride, crystals of saccharose, gelatin spheres or paraffin spheres, or an emulsified liquid that is compatible but is immiscible with the glue and can be absorbed by the tissue relatively quickly to leave pores in the glue. Other suitable biocompatible agents are known in the art. It is contemplated that the tissue can infiltrate the glue matrix and heal across as the glue is being reabsorbed by the body. Adhesive materials may be found within publications known to those skilled in the art and reference made to U.S. Pat. No. 7,044,982 issued May 16, 2006 and U.S. Pat. No. 6,939,364 issued Sep. 6, 2005. Both of which are incorporated herein by reference along with the publications cited therein to disclose and describe surgical adhesives to the extent that these disclosures do not contradict the present disclosure. Examples of glues include, but are not limited to, ArterX® (by Tenaxis Medical, Inc., Mountain View, Calif.), CovaBond® (by Covalent Medical, Inc., Ann Arbor, Mich.), ProGEL VS™ (Neomend, Irvine, Calif.), PPCA & DermaFlex® (by Chemence Medical, Alpharetta, Ga.), Bioglue® (known to be a mixture of bolvine serum albumin and gluderaldehyde, by Cryolife, Inc., Kennesaw, Ga.), Coseal® (by Baxter, Deerfield, Ill.), Microval® (by Medico Corp., Bucuresti, Romania), Omnex® (by Ethicon Inc., Somerville, N.J.), HistoAcryl Blue® (by Aesculap subsidiary of B Braun, in partnership with TissueSeal), Indermil® (by Syneture. Mansfield, Mass.). LiquiBand® (by Advanced Medical Solutions Group, UK), Glubran® (by Gem s.r.l, Italy), GluSeal® (by GluStitch, Canada), Neuroacryl® and TruFill® (by Cordis, Warren, N.J.), and the like. Glues may also include Tissucol® and Tisseel® (by Baxter, Deerfield, Ill.), Avitene® (by Davol, Inc. Providence, R.I.), DuraSeal® (by Confluent Surgical, Waltham, Mass.), Dermabond®, Evicel® and Quixil® (by Ethicon Inc., Somerville, N.J.), LTG® (by MediGlue, Russia), Epiglu® (by Meyer-Haake GmbH Medical Innovations, Germany), TachoSil® (by Nycomed, Austria) and TissuGlue® (by Cohera Medical, Inc., Pittsburgh, Pa.).

II. SOLID MASS COMPOSITIONS

Sol-Gel Composition Moieties

A variety of sol-gel compositions are known in the art, and have various phase transition properties. One will appreciate that various properties may be altered by changing the constituents or constituent ratios in any sol-gel. Persistence properties and mechanical properties may be altered, including the degree to which the present sol-gels liquefy or solidify, the nature or range of phase-transition initiation or stimulus, the persistence and the mechanical properties. The sol-gel may, for example, include particulate materials which may increase the persistence, as further described herein.

The following references disclose processes or compounds useful in this art: U.S. Pat. Nos. 5,525,334; 5,702,361; 5,695,480; 5,858,7465,589,568. Dumortier et al., "A Review of Poloxamer 407 Pharmaceutical and Pharmacological Characteristics" Pharmaceutical Research, Vol. 23, No. 12 (December 2006), pp. 2709-2728. T. G. Park and A. S. Hoffman, "Synthesis, Characterization, and Application of pH/Temperature-sensitive Hydrogels", Proceed. Intem. Symp. Control. Rel. Bioact. Mater., 17 (1990), pp. 112-113. G. Chen and A. S. Hoffman, "Graft Copolymers That Exhibit Temperature-induced Phase Transitions Over a Wide Range of pH", Vol. 3, Nature, 1995, pp. 49-52. S. Beltran, J. P. Baker, H. H. Hooper, H. W. Blanch and J. M. Prausnitz, "Swelling Equilibria for Weakly Ionizable, Temperature-Sensitive Hydrogels", Proc. Amer. Chem. Soc., 1991. J. Zhang and N. A. Peppas, "Synthesis and Characterization of pH- and Temperature-Sensitive Poly(Methacrylic acid)/Poly(N isopropylacrylamide) Interpenetrating Polymeric Networks, Macromolecules, 2000 (currently available on-line on the world wide web). T. G. Park, "Temperature Modulated Protein Release From pH/Temperature Sensitive Hydrogels; Biomaterials 20 (1999), pp. 517-521.

Examples of sol-gel compositions include biocompatible ethylene oxide propylene oxide co-polymers which are typically prepared as block copolymers and are otherwise known as poloxamer or by their tradenames such as Pluronics® or Lutrol®, Polyethylene-polypropylene glycol; Polyoxyethylene-Polyoxypropylene Block Copolymer; Poly(Ethylene oxide-co-Polypropylene oxide), Block; BlockCopolymer of Ethylene Oxide and Propylene Oxide and other names. Examples of poloxamers include poloxamer 118, poloxamer 182, poloxamer 188, poloxamer 237, poloxamer 338, poloxamer 407, other block polymers that can be used in the sol-gel composition include poloxamines, under the tradename Tetronic®, such as Tetronic® 1107, Tetronic® 1307, which are ethylene oxide and propylene oxide based tetra-functional block copolymers. Such polymers are commercially available from a number of sources and can be made by conventional synthetic methods. Other examples of biocompatible sol-gel compositions include, without limitation, block copolymers of polyethylene glycol with a polymer selected from polyester, poly(lactide-co-glycolide), poly(a-hydroxy acids) and poly(ethylene carbonates), described in U.S. Pat. Nos. 7,018,645, 6,004,573 and 5,702,717; poly N-substituted (meth)acrylamides, described in U.S. Pat. No. 5,525,334; modified polysaccharides, such as hyaluronic acid, and others described in U.S. Pat. No. 6,018,033; and copolymers described in U.S. Pat. No. 7,160,931. All of the references are incorporated by reference in their entirety.

In one embodiment, the thermoreversible sol-gel comprises a polymer selected from the group consisting of poloxamer 118, poloxamer 188, poloxamer 338, poloxamer 407, Tetronic® 1107 and Tetronic® 1307 or a mixture thereof, and an aqueous solvent. An aqueous solvent may be water or a water based solution, e.g. an aqueous salt solution, such as a saline solution, phosphate buffered saline, etc suitable for dissolving the polymers.

In some embodiments, the polymer or polymers are present in an amount of about 5% to about 35% by weight.

In some embodiments, the polymer or polymers are present in an amount of about 15% to about 20% by weight.

The molecular weight of the polymer in the sol-gel composition may be in the range of about 8,000 to 16,000, more preferably 10,000 to 16,000, or more preferably 10,000 to 14,000 and most preferably about 12,600. The term "about" as used in this context reflects that commercial preparations of the monomers or polymers as described herein may contain mixtures of varying molecular weights incident to the commercial manufacturing process.

It is contemplated that the transition temperature of a thermoreversible sol-gel composition should be in a range that is tolerable by the organs or tissues of the patient, such as between 0° C. and 45° C. As more fully described herein, the thermo-inducible phase transition may be altered by the addition of a polypeptide or a protein; as such, if proteins are added for biological activity (such as a protein having therapeutic effect), the practitioner will note that the phase-transition property of the underlying polymer may be altered. Alternatively, the protein may be added to effect a change in transition temperature of a composition otherwise having the requisite modulus. Such proteins are non-therapeutic and preferably non-immunogenic. In one embodiment, the protein is albumin such as BSA or HSA. Recombinant versions of such proteins (or any proteins as described herein) may be preferred for commercial manufacturing reasons, for assurance of no animal-originating pathogenic agents.

Phase-reversible sol-gel compositions whose phase transition is triggered by other stimuli, such as pH, ionic strength, electrical field, magnetic field, electromagnetic field, osmolarity, solvent composition, light, ultraviolet light, pressure, chemical composition, concentration, and combinations thereof can also be used in the methods of the invention. Examples of such sol-gel compositions are described in, e.g., U.S. Pat. No. 5,252,318 (Joshi et al), U.S. Pat. No. 5,939,485 (Bromberg et al), and US patent publications 2004/0096508 (Gutowska et al), US 2004/0213756 and 2004/0208845 (both by Michal et al), which are incorporated by reference in their entirety. For Example, chitosan solutions which undergoes a phase transition at a pH of about 7.0, and compositions that undergo phase transition when triggered by at least two stimuli are described therein. Dilution of the composition can facilitate phase transition in certain cases.

Other compositions useful as the solid mass in this invention include a variety of hydrogels, which are water-insoluble three-dimensional networks that formed by the cross-linking of water-soluble monomers. Either synthetic or natural polymers may be used. Useful synthetic materials are poly(lactic acid) (PLA), poly(glycolic acid) (PGA), and their copolymers, poly(lactic co glycolic acid) (PLGA). Such compositions are well known in the art.

In situ cross linking (and/or polymerization) can be used to form the gel or to increase rigidity. Therefore, for anastomosis of an individual, the crosslinking is able to take place under physiologic conditions. Particularly for human uses, physiological conditions involve a temperature of about 37° C., and a pH of about 7.4. Suitable cross linking conditions will be chosen based on the chemical structure of the monomers to be polymerized, the desired mechanical and persistence properties of the hydrogel after polymerization, and other considerations as are well known in the art.

In one embodiment, the sol-gel composition is delivered into at least a portion of the distal end of the lumen in a solid form. In some circumstances, it is preferable that the delivered composition protrude from the lumen thereby providing a mating mechanism for the distal end of the other lumen so that aligning the distal ends of the two lumens is relatively easy.

Waxes

Other solid mass materials useful in this invention include biocompatible waxes.

The term "wax" as used herein means a relatively low-melting temperature, high-molecular-weight, organic mixture or compound, similar to fats and oils but lacking glycerides. See, Dorland's Medical Dictionary (2004, W.G. Saunders, herein incorporated by reference for various definitions under the "wax" listing).

As noted by Dorland's, waxes may originate from natural sources (e.g., insects or plants) or may be synthetics, and most are fatty acid esters and alcohols with some hydrocarbons. Other moieties may include lauric acid, myristic acid, palmitic acid, stearic acid, arachidic acid, lignoceric acid, palmitoleic acid, oleic acid, linoleic acid, linolenic acid, arachidonic acid and other biocompatible fatty acids that are endogenous to the treated patient as well as mixtures thereof.

The materials are not all-inclusive, and the principal useful feature herein is the ability of the wax to be "melted" or substantially liquefied with heat or dissolved in the body fluid once flow is reinstated, particularly in situ, at temperatures which are not injurious to live tissue (if used pursuant to a surgical procedure on a live patient). The melting point of the waxes can be adjusted by conventional melting point depression by mixing two or more waxes together. For example, lauric acid has a melting point of 44.2° C. and slight depression of this melting point by mixing with another suitable fatty acid can bring the melting point down to 40 to 42° C. Low temperature polyester waxes, such as "Steedman's wax" which have a melting temperature of about 37° C. (human body temperature) may be used in some circumstances. See, Steedman, H. F., Nature 179:1345 (29 Jun. 1957).

In one embodiment, the wax can be preformed into a "stick" configuration of predetermined diameters. The clinician can then insert a portion of the wax into a first lumen with the remaining portion providing a mating mechanism for the distal end of the other lumen so that aligning the distal ends of the two lumen is relatively easy.

For microsurgical techniques involving human or other mammalian blood vessels, the diameter of between about 0.5 and 1.5 mm is probably suitable. For other purposes, such as intestinal anastomosis or large venous surgeries, the diameter may be several centimeters ("cm"). (Although the term "diameter" is used, if the biocompatible stick is not cylindrical, the area of the surface of the terminus is the relevant measurement for determining what will fit into distal termini of tubular tissue.)

Thixotropic Agents

Still other solid mass materials useful in this invention include thixotropic or other non-Newtonian fluidic agents. These materials use deformation, or shear stress, for phase change along the solid to fluid (or vice versa) continuum.

In general, for fluids demonstrating non-Newtonian dynamics, viscosity changes with applied stress or applied shear rate. Thixotropic, or other non-Newtonian fluids, become more or less viscous with applied movement. For example, some thixotropic agents become less viscous subjected to stresses above a critical level. These shear-thinning fluids may be inserted into immobilized tubular tissues to stabilize the distal ends as described herein. Upon joining, movement may be applied to the now-sealed tissues to liquefy the thixotropic agent. These stresses may be applied externally or may arise naturally from the peristaltic pressure in the circulatory system. Thixotropic agents include various bioabsorbable or dissolvable clays, materials with corn starch or other carbohydrate-based materials, and other colloidal and other materials as are available to those of skill in the art. It is contemplated that the thixotropic agents suitable for use in the present invention will have a yield stress of from about 100 to about 500,000 Pascals, preferably from about 8,000 to about 50,000 Pascals or 10,000 to about 50,000 Pascals, and even more preferably from about 12,000 to about 40,000 Pascals.

Thus, as thixotropic agents are used herein for their relatively solid form in supporting distal termini in tubular tissues, it may be initially deployed in a less viscous state, and allowed to "rest" or not be subject to shear-thinning movement. Upon satisfactory adjoining of the tissues, shear-thinning stress may be locally applied.

Additional Moieties

The solid mass compositions used in the methods of this invention may include one or more additional moieties. For example, a biologically functional agent, a dye and/or a contrasting agent may be added to the solid mass to provide additional functionalities for the solid support.

Biologically active moieties or agents may include, without limitation:
- antithrombotic agents, such as coagulants (for example heparin), platelet inhibitors, and thrombolytic agents;
- anti-anginals, such as beta-blockers, calcium channel blockers, and nitrates;
- antiinfectives, such as antibiotics, antiviral and antifungal agents;
- analgesics and analgesic combinations;
- antiinflammatory agents;
- antiarrhythmics;
- antihypertensives;
- heart failure agents;
- wound healing agents;
- antiasthmatic agents;
- antidiuretic agents;
- antineoplastics;
- antipyretics;
- antispasmodics;
- anticholinergics;
- immunosuppressives;
- sympathomimetics;
- central nervous system stimulants;
- parasympatholytics;
- hormones such as growth hormones, estradiol and other steroids, including corticosteroids;
- muscle relaxants;
- lipid lowering agents;
- anti-ulcer H2 receptor antagonists,
- anti-ulcer drugs;
- anorexics;
- antiarthritics;
- sedatives;
- tranquilizers;
- anti-restenosis agents;
- anti-proliferatives, such as everolimus, sirolimus, paclitaxel, rapamycin and biolimus (Biosensors International, Singapore);
- pro-angiogenic agents;
- proteins—for example, growth factors, gene vectors containing growth factors, such as fibroblast growth factor (FGF), insulin-like growth factor (IGF), vascular endothelial growth factor (VEGF), B-cell growth factor (bGF), hepatocyte growth factor (HGF), monocyte chemotactic protein-1 (MCP1), and those described in U.S. Pat. No. 6,702,744 (Mandrusov et al), which is incorporated by reference in its entirety. The proteins may be in protein or gene form, or combinations thereof, and
- gene-therapies.

Examples of the above biologically active agents and other agents suitable for use in the solid mass are described in, for example, U.S. Pat. No. 6,702,744 (Mandrusov et al), U.S. Pat. No. 7,169,404 (Hossainy et al), U.S. Pat. No. 6,908,624 (Hossainy et al), U.S. Pat. No. 6,899,729 (Cox et al), U.S. Pat. No. 7,169,178 (Santos, et al), all of which are incorporated by reference in their entirety.

The biologically active moiety may be optionally formulated in sustained release or in gene vectors.

The biologically active moiety may optionally be therapeutically effective as administered, and the subject solid mass may optionally contain a therapeutically effective amount of the biologically active moiety.

A therapeutically active moiety will be a biologically active moiety. A therapeutic effect is one which seeks to treat the source or symptom of a disease or physical disorder. The term "treat" or "treatment" as used herein refers to: (i) preventing a disease or disorder from occurring in a subject which may be predisposed to the disease or condition but has not yet been diagnosed as having it; (ii) inhibiting the disease or disorder, i.e., arresting its development; and/or (iii) ameliorating or relieving the disease or disorder, i.e., causing regression of the disease. A therapeutically effective amount is sufficient to establish causation of a therapeutic effect, as determined by relevant clinical standards. The therapeutically effective amount will vary depending upon the specific agent incorporated, the subject and disease condition being treated, the weight and age of the subject, the severity of the disease condition, the dosing regimen to be followed, timing of administration, the manner of administration and the like, all of which can be determined readily by one of ordinary skill in the art.

Biologically active moieties may also be incorporated into the ligation (joining) composition applied to the tubular tube tissue so adjoined incident to the anastomosis. As described herein, ligation can be accomplished any number of ways, and, if the present anastomosis materials are used, sutures or an adhesive may be most practicable.

Contrast agents, such as a biocompatible radio opaque material capable of being monitored by, for example, radiography, may also be added to the solid mass to track and monitor the solid mass and/or the procedure. The contrast agent may be water soluble or water insoluble and preferably does not contain radioactivity above the native or endogenous amounts naturally occurring in the elements employed.

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 microns or less. Other water insoluble contrast agents include gold, tungsten, and platinum powders.

The solid mass compositions may also include a suitable biocompatible dye for visualization, especially when a lumen has a thick wall. Such dyes are well known in the art.

III. ANASTOMOSIS METHODS

It is contemplated that the present invention can be applied to any anastomotic procedure that connects one hollow tissue structure (lumen) to another hollow tissue structure (lumen), such that the spaces within each hollow tissue structure are connected thereby forming a conduit (an intraluminal conduit). It can be used in a microvascular context, which is performed between ends of blood vessels in the course of, for example, reattaching severed body parts and/or transplanting organs or tissue. It can also be used in minimally invasive procedures or percutanteous approaches with catheters. It can be used to connect non-conjoined lumens arising from surgical procedures wherein the originally intact lumen has been severed for the purposes of, e.g., removing a blockage or partial blockage. Suitable lumens include, by way of example, the vasculature, the vas deferens, the fallopian tubes, the urinary tract, tear ducts, bowel, mammary glands, alimentary ducts, pancreatic ducts, bile ducts, etc. (Specific anatomical lumens may be referenced by their conventional anatomical nomenclature such as tubes, ducts or vessels, as used in context herein.)

In one embodiment used for illustrative purposes only, the anastomosis is performed during coronary artery bypass graft (CABG) procedures or peripheral bypass procedures to connect two blood vessels or one blood vessel with one synthetic graft. The blood vessels connected together may have different diameters. Further one or both of the vessels may be very small, and may be on the order of about 1 to 5 millimeters ("mm"). The microvascular anastomosis procedure using the present invention may be performed under a microscope.

Referring now to the Figures, the invention is described schematically and in a simplistic fashion in order to convey the general concepts. With these concepts in mind those skilled in the art will contemplate detailed specific embodiments of the invention which are intended to be encompassed by the present claims. FIG. 1 shows a schematic cross-sectional view of a lumen which may be a vessel 1 which has flow 2 running there through. A portion of the vessel indicated by points 3 and 4 has a restricted flow due to the formation of blockages 5 and 6. The blockage may become so severe that the flow is completely blocked. Those skilled in the art will appreciate that a range of different treatments are available for restoring flow.

Prior to the operation to restore flow, the vessel needs to be occluded to stop the fluid (e.g., blood) flow. Such occlusion is important for anastomosis involving a blood vessel to prevent excessive loss of blood and complications caused by a continuous blood flow. This can be achieved by applying at least one clamp on the blood vessel to be operated on or by conventional means, such as applying a pressure on the blood vessel or providing a vessel loop or vessel tie so that the blood flow is stopped or reduced. However, clamping may not be necessary for anastomosis of other types of lumens where there is no continuous flow of fluid or the amount of fluid does not complicate the procedure.

Figure 2:
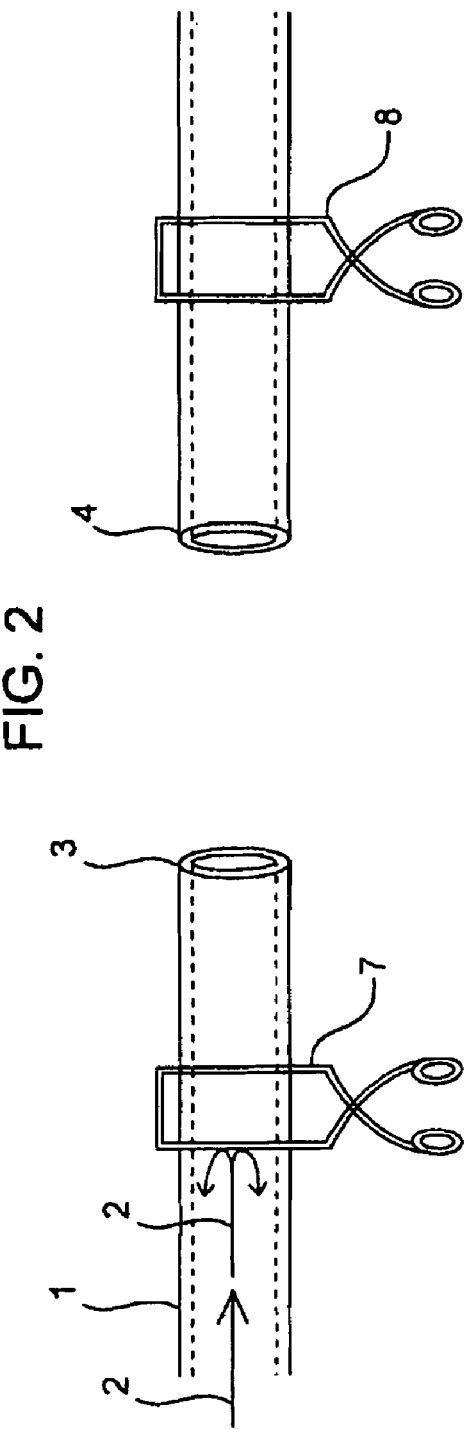
FIG. 2 is a schematic cross-sectional view of the tubular tissue of FIG. 1 wherein the area having the partial blockage has been removed creating two non-conjoined lumens having both ends of the tubular tissue clamped off.

Thus, as shown in FIG. 2, clamps 7 and 8 have been placed on the vessels to stop the blood flow in the section between the clamps prior to removal of the blocked section. Such clamps can be any surgical clamps suitable for clamping the vessels to be operated on from the outside, such as clamps, clips and tourniquets or snares. After clamping, a portion of the vessel 1 which has the restricted flow between the points 3 and 4 is then surgically removed. Those skilled in the art will understand that the distance between the points 3 and 4 is sufficiently small such that the ends can be brought into contact with each other to restore flow.

In some embodiments, after the vessel is cut into two non-conjoined vessels with open ends or after the diseased portion is severed, or in the case of end-to-side or side-to-side anastomosis after a hole is created on the vessel, the part of the vessel between the clamp 7 and the open end 3 can be flushed with a biocompatible fluid, such as water or an isotonic saline solution, to remove any undesired matter, such as diseased or dead tissue or cells, mineral deposits, plague, thrombus, blood clots, etc., that may be present in the vessel. In one embodiment, the solution is sterile.

Figure 3:
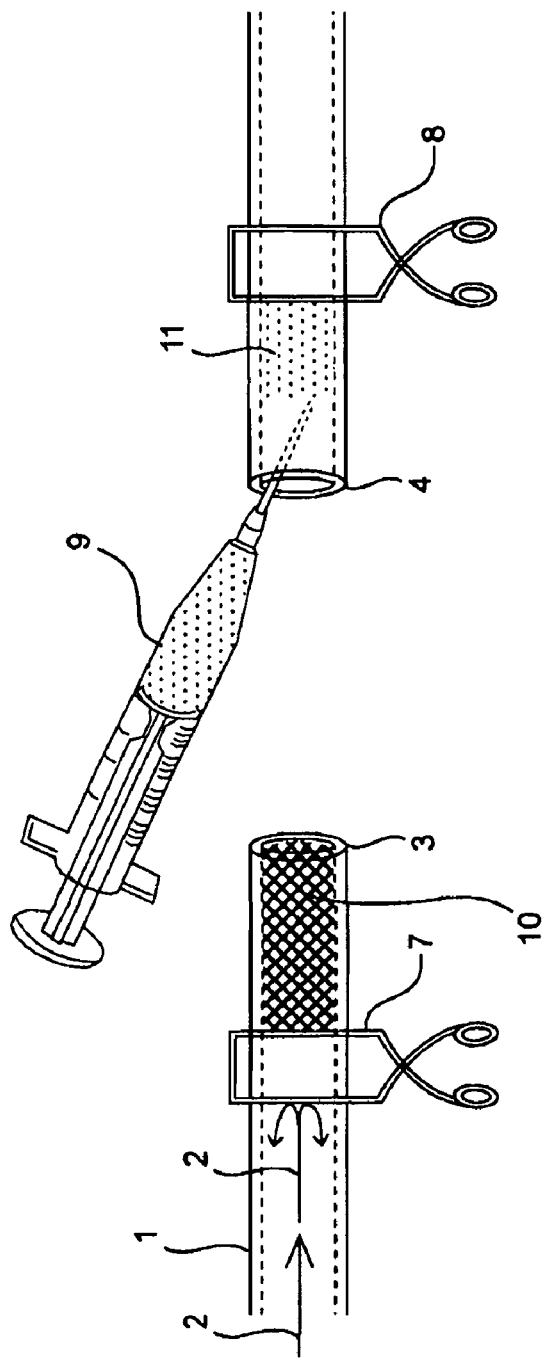
FIG. 3 is a schematic cross-sectional view of the tubular tissue of FIG. 1 with one end filled with thermoreversible sol-gel (solid or gel phase) and the other end being filled with the sol-gel (liquid phase) via a syringe.

Referring now to FIG. 3, the inside of the vessel 1 between the clamp 7 and the end 3 has been filled with the phase-reversible sol-gel 10 which is shown in solid phase by the crossed markings. The area between the clamp 8 and the end 4 is being filled with sol-gel 11 in a liquid phase. In an optional embodiment, the thermoreversible sol-gel 10 can be introduced in its gel phase so as to ease delivery into the vessel. The sol-gel is injected from a suitable source such as a hypodermic needle 9. When the sol-gel material is in the hypodermic needle it may be either in a flowable liquid phase or in a gel phase. In the former case, the composition will undergo a phase transition to a solid gel phase (10) upon the application of the suitable environmental stimuli such as heat. In the latter case, the composition is delivered in a solid gel phase (10) and maintained in that phase by continuing the application of the suitable environmental stimuli such as heat. It is contemplated that the later is more convenient when the sol-gel composition has a lower transition temperature, for example, a transition temperature of less than 30° C.

It is contemplated that additional amount of the sol-gel composition may be applied to the lumens during the joining step if needed.

Alternatively, the procedure includes approximating the lumens in a connecting position, such as by partially suturing the two lumens. For example, a few sutures can be applied on the opposite sides of the lumens to bring the lumens in a connecting position. The thermoreversible sol-gel composition can then be applied to the partially sutured opening and form a continuous gel column to fill the lumens to give the structural support for the subsequent procedure that completely joins the lumens. The amount of the sutures applied for this purpose is not intended to fully join the lumens but is to keep the lumens together so that the gel can be applied to both lumens together, for example, in some embodiment, the sutures are 4-6, or 2-4 and preferably 1-2 sutures on each side. Approximating the lumens can also be preformed by using temporary or permanent anchoring clamps or clips, laser, electrocautery, etc, that are known in the art to connect lumens.

Alternatively, partial suturing can be applied after application of the gel (making sure there is no twists on the lumen) and before application of the glue. For example, the vessels which are deflated due to clamping and lack of blood flow can be inflated with application of a gel. Suture can then be applied to the inflated vessels to partially connect them to bring them in a connecting position before a glue is applied to completely and permanently joining the vessels. The lumens can also be partially ligated by using temporary or permanent anchoring clamps or clips, laser, electrocautery, etc, that are known in the art for connecting lumens.

The sol-gel material is included in a sufficient amount so as to maintain at least a portion of the distal end of vessel 1 open. In the absence of some force, the side walls of the vessel 1 will contact each other and cause the vessel to close in the absence of flow through the vessel. The solid gel phase (10) imparts sufficient structural rigidity to the lumen to permit the anastomosis to proceed with the vessel in its fully filled form.

Figure 4:
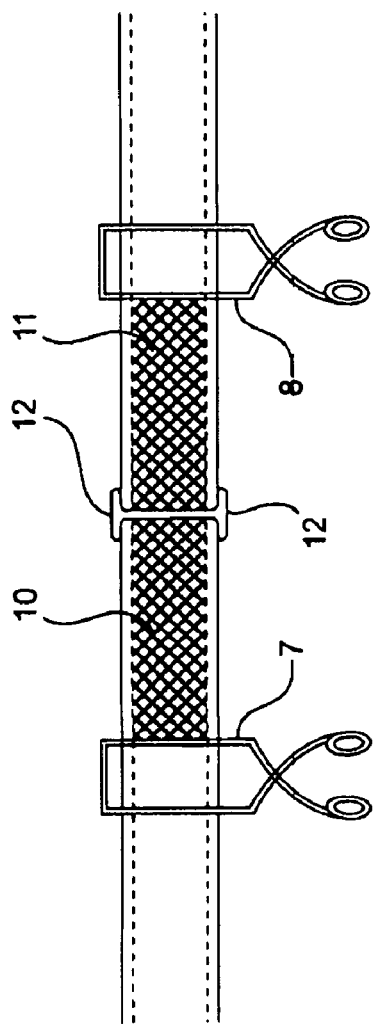
FIG. 4 is a schematic cross-sectional view of the tubular tissue of FIG. 1 with the ends sealed, the gel (solid phase) in place and the clamps still present.

As shown in FIG. 4, the two lumens can be joined by applying an adhesive or glue 12 on the two ends of the lumens as well as on the outer surface of the vessel at points 3 and 4 and sealed together. Although FIG. 4 shows the use of a glue, it is to be understood that as described herein, joining or ligation can be accomplished any number of ways, and, if the present anastomosis materials are used, sutures or an adhesive may be most practicable. Sutures are well known in the art as are surgical glues or adhesives. Such glues are biocompatible and are generally cyanoacrylate-based adhesives, fibrin-based adhesives, polyurethane-based adhesives, polyisocyanate-based adhesives, polyethylene glycol-based glues, latex glues, biologics glues or protein-based glues, and UV curable glues. Suitable glues include but are not limited to the glues described herein. The suture or glue may contain biologically active moieties such as antimicrobial agents (e.g., U.S. Pat. No. 5,762,919) or other agents described herein.

Due to the presence of the gel (in solid phase) significant amounts of adhesive can be used without resulting in vessel closure. In the absence of a structural support, such as the phase-reversible sol-gel 10 in this example, being present within the vessel the application of pressure to the outside of the vessel such as by the application of glue can cause collapse of the vessel. However, since the phase-reversible sol-gel 10 is holding the vessel open, glue can be applied liberally not only to the ends 3 and 4 which are to be sealed together but the glue 12 can be applied along the surface of the vessel 1 near the point where the seal is to take place. Thus, as shown in FIG. 4, glue has been applied on the outside of the vessel 1 on either side of the point where the ends are sealed. The glue can extend outward in any desired amount. However, with smaller vessels extending the glue out a distance of about 1 mm to about 10 mm is generally sufficient. The glue can extend outward around the entire circumference of the connecting point.

After the adhesive 12 has been allowed to cure and seal bonds between the two ends of the vessel, the clamps 7 and 8 can be removed. In one embodiment the glue also penetrates inward to the surface of the gel thereby providing adherence of the entire tissue cross-section of the first lumen to the second lumen. In another embodiment, the glue is applied not only to the outer surface but also to the cross-sectional surfaces of the lumens to be closed. It is contemplated that the glue may be porous to allow tissue ingrowth and healing across the barrier. For example the glue may contain a porogen which may be an emulsified liquid that is compatible but is immiscible with the glue and can be absorbed by the tissue relatively quickly to leave pores in the glue. It is contemplated that the tissue can infiltrate the glue matrix and heal across as the glue is being reabsorbed by the body. The glue may further comprise a biologically active agent as described herein to facilitate tissue growth, prevent or reduce inflection, restenosis, and other conditions that may be associated with such procedures.

In a still further embodiment, a solid mass, such as a sol-gel, has a superior wetting characteristic to the vessel when compared to the glue, to inhibit the glue from penetrating into the inner surface of lumen. In some embodiments, the glue and the sol-gel have limited miscibility. When the vessel is not supported by a solid mass, such as a sol-gel, connecting two vessels with glue may cause safety concerns due to the possibility that the glue may seal the inside of the lumen. In some embodiments, the glue and the sol-gel are substantially immiscible.

The lumens may also be joined by using laser, such as laser welding or laser soldering. See, e.g., D. Simhon, in Lasers in Surgery: Advanced Characterization, Therapeutics, and Systems XIV, Vol. 5312, 176-185 (2004); S. Nakata, et al, *The Journal of Thoracic and Cardiovascular Surgery*, 98, 57-62, 1989; and Sanford L. Klein, et al, *Microsurgery*, 15:4, 287-288, 2005. However, laser anastomoses have been reported to cause side effects such as soldering the lumen shut, hemorrhage and degeneration of collagen and protein in the adventitia and media, and under conventional laser anastomosis conditions. See, e.g., S. Nakata, et al, *The Journal of Thoracic and Cardiovascular Surgery*, 98, 57-62, 1989; T. Bavbek, et al, *Opthalmologica* 219, 267-271, 2005. It is contemplated that placing a solid mass, such as a sol-gel composition, inside the lumens will help to keep the end of the lumen open and protect the tissue from being damaged by laser. The lumens may also be joined by using electrocautery or other means known in the art.

Figure 5:
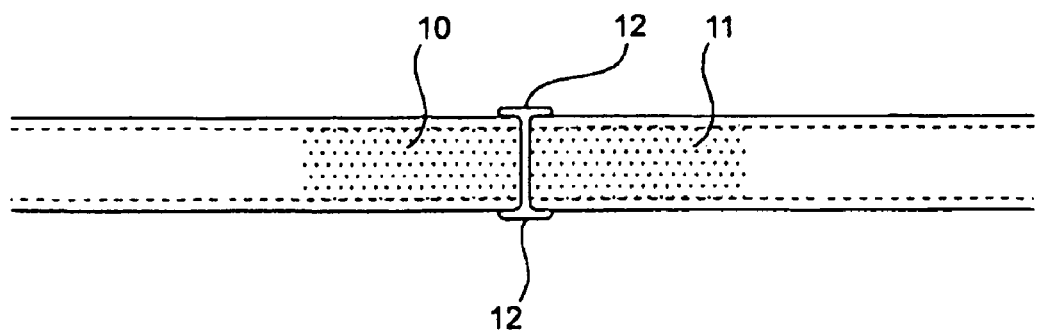
FIG. 5 is a schematic cross-sectional view of the tubular tissue of FIG. 1 with the ends sealed, the sol-gel (reversed to liquid phase) in place and the clamps removed.
Figure 6:
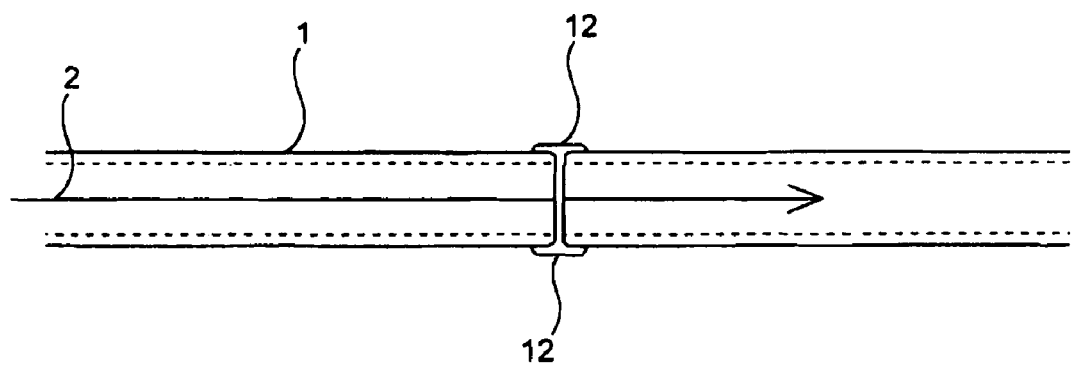
FIG. 6 is a cross-sectional view of the tubular tissue of FIG. 1 showing the sol-gel dissolved and flow restored with the blockage area removed.

Turn to FIG. 5, when the clamps 7 and 8 are removed, the stimuli such as heat which was being applied to maintain the gel in a solid state is removed and gel changes phase to a liquid. Once the gel reverses its phase change to become a liquid and the blood flow against the liquefying gel causes the gel to be dispersed, the vessel reopens as shown in FIG. 6.

In the case where the sol-gel composition has a transition temperature at or below the body temperature, such as from about 0° C. to about 35° C., the transition of the sol-gel composition from the solid state to the liquid state can be induced by cooling the connected vessel by, for example applying cold water, a cold saline solution or ice.

In the case where the sol-gel transition stimulus is ionic strength, the phase change may be induced by allowing the blood, which may have a different ionic strength than the gel, to flow to the gel and induce the phase transition from a gel to a liquid.

In the case where waxes are employed, heat can be applied to the joined lumens to melt the wax. Moreover, if the clamps are removed prior to application of heat, both melting and dissolution of the wax into the body fluid can occur.

In the case where thixotropic agents are employed, the application of shear stress to the mass, such as gentle squeezing of the joined lumens or the stress arising from the pumping action of the heart, will significantly reduce the viscosity of the mass and render it flowable with the body fluid.

Figure 5A:
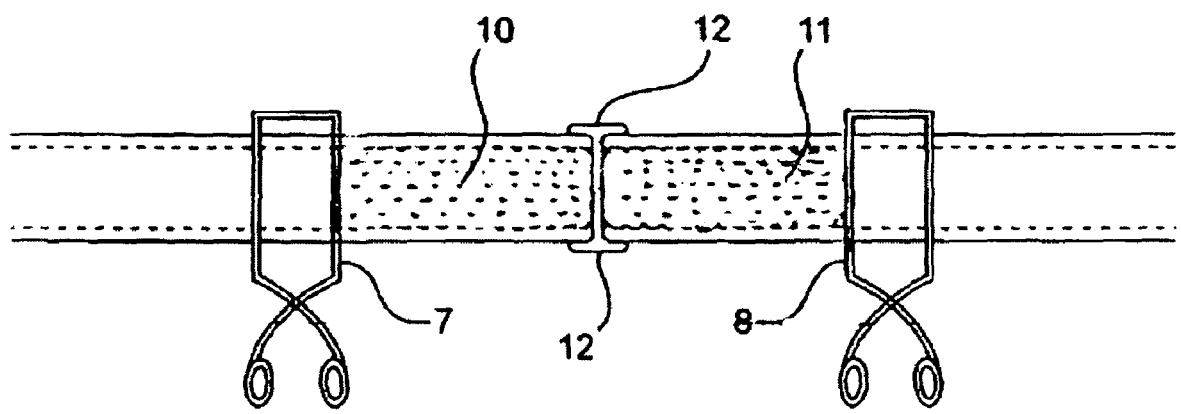
FIG. 5A is a schematic cross-sectional view of the tubular tissue of FIG. 1 with the ends sealed, the sol-gel (reversed to liquid phase) in place and the clamps still present.

In some embodiments, after the lumens are connected and before the clamps are removed, the gel is changed to a liquid state by applying an appropriate stimulus, as shown in FIG. 5A. For example, in the case of a thermoreversible sol-gel, the gel is changed to the liquid state by lowering the temperature to below the transition temperature by removing the heat source or by applying a cold source, such as cold water or ice. The operating physician then confirms that the phase transition is complete, for example by observing the vessel or by waiting for a sufficient amount of time, to ascertain that no undesired solid mass remains in the vessel which may cause safety concerns. After confirming that all solid mass has become a liquid, the clamps 7 and 8 are then removed to allow establishment of blood flow and subsequent removal of the liquefied solid mass by the blood flow. The phase transition can be done before or after the glue is cured or hardened, preferably after the glue is cured or hardened.

At this point as shown in FIG. 5, the glue 12 has cured or hardened. The glue 12 seals the ends of the vessels together but also is applied to the outer surface of the vessel on either side of the point of connection where it is circumferentially applied. Accordingly, when the glue 12 hardens the glue 12 acts as an external stent holding the vessel 1 open after the gel has liquefied. Although it is not necessary to have the glue forming the external stent, this can provide an additional advantage. The glue may be designed so that it remains in place for a considerable period of time or designed so that it dissolves slowly over time as the two ends of the vessel grow together.

Those skilled in the art will understand that particularly high temperatures will not be useful for treating a patient as this may cause undue heat damage to live tissues. It is contemplated that sol-gel compositions with a transition temperature of between 0° C. to 45° C. can be used in the methods of this invention. In particular, a transition temperature of around 42° C. to maintain the gel in the solid state might be used provided the gel will revert to its liquid state at around body temperature or 37° C. It is contemplated that a sol-gel having a transition temperature that is lower than the body temperature, such as from 0° C. to 35° C., or from 15° C. to 35° C., can also be used. In such a case, the gel can be converted to its liquid state by lowering the temperature of the anastomosis site to below the transition temperature by cooling, for example, with ice or cold saline or phosphate buffered saline.

In this particularly described embodiment, temperature is used as the mechanism for causing the gel to undergo a phase change. However, as indicated above, other factors such as pH, ion concentration such as calcium ion concentration, concentration of the composition, pressure, electric field, magnetic field, electron magnetic radiation, light or ultraviolet light, osmolarity, ultrasound, and the like and combinations thereof can be used. For example, some sol-gel compositions are at a gel state in solution with a high ionic strength but undergo a phase transition to the liquid state when the ionic strength is reduced. Thus, it is contemplated that a gel composition having a high ionic strength, e.g. a hypotonic composition, can be injected to the lumens to be joined and upon joining the lumens, the ionic strength can be reduced when the clamps are removed and blood flow enters into the area of the ligation, causing the gel composition to liquefy.

Additionally, the gel may be removed by dissolving in the body fluid or by a combination of dissolution and a phase transition. For example, the gel may dissolve in blood once the clamps are removed and blood flow enters into the area of the ligation.

Regardless of the particular parameter used to undergo the phase transition, the formulation will take into consideration factors such as the normal temperature, normal pH, normal ion concentration of the subject being operated on. In one embodiment, the gel will be in a liquid phase when the parameter such as temperature, pH or calcium ion concentration is at or very close to that of the surrounding environment and will be in a solid or gel phase when it is raised somewhat above or below the normal point but not sufficiently far from normal so as to be damaging to the tissue. Thus, high temperatures, extremely high or low pHs, as well as very high or low ion concentrations, would not be used, as such would likely cause damage to the surrounding tissue. When electric field is used as the trigger, the electric voltage and current needed to effect a phase transition should be minimal, specially in cases where the cells and tissues may be very sensitive to a change in electric field, such as in a cardiovascular surgery.

Other aspects of the above method include visualization or imaging of the joining of the lumens and various aspects of procedure as well as monitoring and evaluating the safety and effectiveness of the procedure. In many cases, the procedure is performed under a condition that requires a visual aid in order for the physician to monitor or visualize the progress of the procedure. For example, a magnifying glass is often needed in an anastomosis procedure. In the microvascular context, an operating microscope is often used and a laparoscope is used in a laparoscopic procedure. Other imaging medical instruments may also be employed to monitor the progress and/or the effectiveness of the procedure, including but not limited to collecting blood samples to measure the serum concentration of biomarkers indicative of myocardial performance or the performance of other organs connected to the lumens being conjoined, such as measuring troponin T levels in a coronary artery bypass grafting procedure, measuring the diameters of the conjoined lumens using, for example CT angiography, determining patency and flow through, for example ultrasonic Doppler imaging (e.g., using a visual sonic machine), and/or monitoring the presence of the liquefied solid mass in the serum or urine. Suitable methods are generally known in the art.

It has been demonstrated in mammalian experiments, that by performing an anastomosis procedure using the method and composition of the present invention, the time required to connect the blood vessels is significantly reduced to an average of 3 minutes 11 seconds (ranging from 55 seconds to 6 minutes), from an average of 29 minutes 15 seconds (ranging from 20 to 49 minutes) with conventional hand-sewn anastomosis procedures. See Example 1. This in turn resulted in improved outcomes of the procedures in terms of the diameters and patency rates of the vessels connected, complications caused by the procedures and the mortality rates of the subjects treated. See Example 1. Further, the experiments showed that anastomotic flow and burst strength at six weeks after the anastomosis procedures using the present invention were about the same if not better than using conventional hand-sewn procedures.

The methods of this invention can be applied to end-to-end, end-to-side, and side-to-side anastomosis. It can be used to join two or more blood vessels in a patient, or join a blood vessel of the a patient with a lumen selected from the group consisting of arteriovenous graft, arteriovenous shunt, allograft, xenograft, synthetic graft, and cadaver xenograft.

It is contemplated that the methods of the present invention are useful in other medical procedures, such as reversal of vasectomy, reversal of fallopian tube ligation, and reconstructive tubal surgeries to treat blocked or damaged fallopian tubes. The method can also be used to connect an AV graft or AV shunt or fistula to a blood vessel for hemodialysis as well as for bypass strategies for below the knee bypass, such as in the treatment of a peripheral arterial disease. Further the method of the present invention can be used in alimentary anastomosis. Significant leak rates (about 2-5%) have been resulted by current alimentary anastomosis procedures. Many of the leak incidents are fatal or lead to significant morbidity. Because the alimentary tubes being ligated can be supported inside by the sol-gel of the present invention and the glue can be applied circumferentially outside the point of connection, thus allowing complete sealing, it is contemplated that anastomosis using the method of the present invention will significantly reduce the leak rate and lead to decreased mortality and morbidity caused by alimentary anastomosis. The methods and compositions of the present invention can also be used in the treatment of conditions involving urinary tracts, tear ducts, bowel, mammary ducts, pancreatic ducts, bile ducts, and the like.

IV. KITS OF THE INVENTION

One aspect of this invention is in the form of a kit of parts. The kit may include specific instructions with respect to how to carry out the methodology of the invention as exemplified above.

Further, the kit may include a container containing the biocompatible solid mass or solid mass precursor e.g., the solution phase of a sol-gel composition, preferably in sterile form, and a delivery device. The delivery device may be a syringe, a pipette or tweezers, catheter or laparoscopic tool, and the like. Alternatively, the kit may contain a delivery device loaded with a flowable form of the solid mass material of the type described above, again preferably in sterile form. For example, the kit may contain a syringe already loaded with a sterile sol-gel composition or an ampule made from glass or plastic that contains a sterile sol-gel composition, and which has a tip that may be cut open to apply the sol-gel contained therein.

When a solid mass material is provided in the kit, it can be in a rod form of defined diameter so as to match the diameter of the lumen to which the solid mass is to be inserted.

Still further, the kit may include one, two or more clamps of the type which might generally be used in connection with the lumen or type of vessel (or duct, tube, etc.) being treated. Still further, the kit may include sutures, anchoring clamps or clips, or surgical glue of the type described above. Still further, the kit may include a triggering component or element which, when activated, results in phase transition of the sol-gel material. For example, the triggering component may be a component which when activated generates heat, cold or other triggering conditions, which can be used to induce the gel-formation and/or maintain the sol-gel in its solid or gel like phase until it is to be removed or it may trigger a gel to liquid transition. Such triggering elements may include, but are not limited to, a heat source, such as a heated air blower capable of delivering warm air, and heating pads, an infrared heating apparatus, etc, that can maintain a temperature sufficient to induce the change of phase of the thermoreversible sol-gel; a cooling source; a light energy source; an electric source; an ultrasound source; an irrigated liquid stream source; or sources to generate other triggers described herein. Further, the delivery device may be coupled with a triggering element, such as a heating or cooling component, and serves as both a delivery device and a triggering element. The kit may further include an adhesive delivery system.

The kit may further include one or more pharmaceutically active drugs which may be separate from or incorporated into the solid mass or its liquid precursor. Thus, for example, the drug which may be provided separately in the kit or incorporated into the solid mass or its liquid precursor may include an anticoagulant such as heparin. The solid mass or its liquid precursor may further include an antibiotic or other material such as a wound healing medicament which aids in healing of the vessel.

Commercially, for ease in practical application, materials may be prepared so that they are sterile and substantially pyrogen free, for example, in accordance with regulatory requirements. Materials and devices may be prepackaged in sterile packaging.

V. EXAMPLES

Examples 1-3 and 8 are working examples demonstrating the practicability of the present invention. Example 1 demonstrates that, for a thermoreversible composition, gelation temperature may be optimized by the addition of an additional moiety. Example 2 demonstrates the practicability of the present invention in an anastomosis animal model, demonstrating improved results over traditional methods in terms of increased body fluid flow and decreased mortality, in preliminary results. Example 3 demonstrates the additional aspect of use of the present methods and compositions for sustained delivery of a biologically active molecule, here, heparin, the blood thinner. Examples 4-7 and 9 are prophetic examples of practicability in human anastomosis procedures.

Example 1

Changing the Sol-Gel Transition Temperature of a Thermoreversible Sol-Gel Composition with the Addition of a Protein One embodiment of the present invention relates to exploitation of the sol-gel transition temperature of thermoreversible sol-gel compositions, and this working example demonstrates how the gelation temperature may be altered to be slightly above the normal body temperature. Therefore, this example allows a sol-gel material to assume a gel state inside the distal portion of the lumen when the temperature is temporally raised to above the transition temperature so that the geometry of the distal portion of the lumen is stabilized during the anastomosis procedure. After the anastomosis procedure, the temperature is returned to normal body temperature, which is below the transition temperature of the sol-gel material, so that the sol-gel material liquefies and becomes flowable in the conjoined lumen. This working example demonstrates that with an appropriate concentration of a protein, here bovine serum albumin, the gel-transition temperature of a thermoreversible sol-gel can be modulated to be slightly above the normal body temperature.

Figure 7:
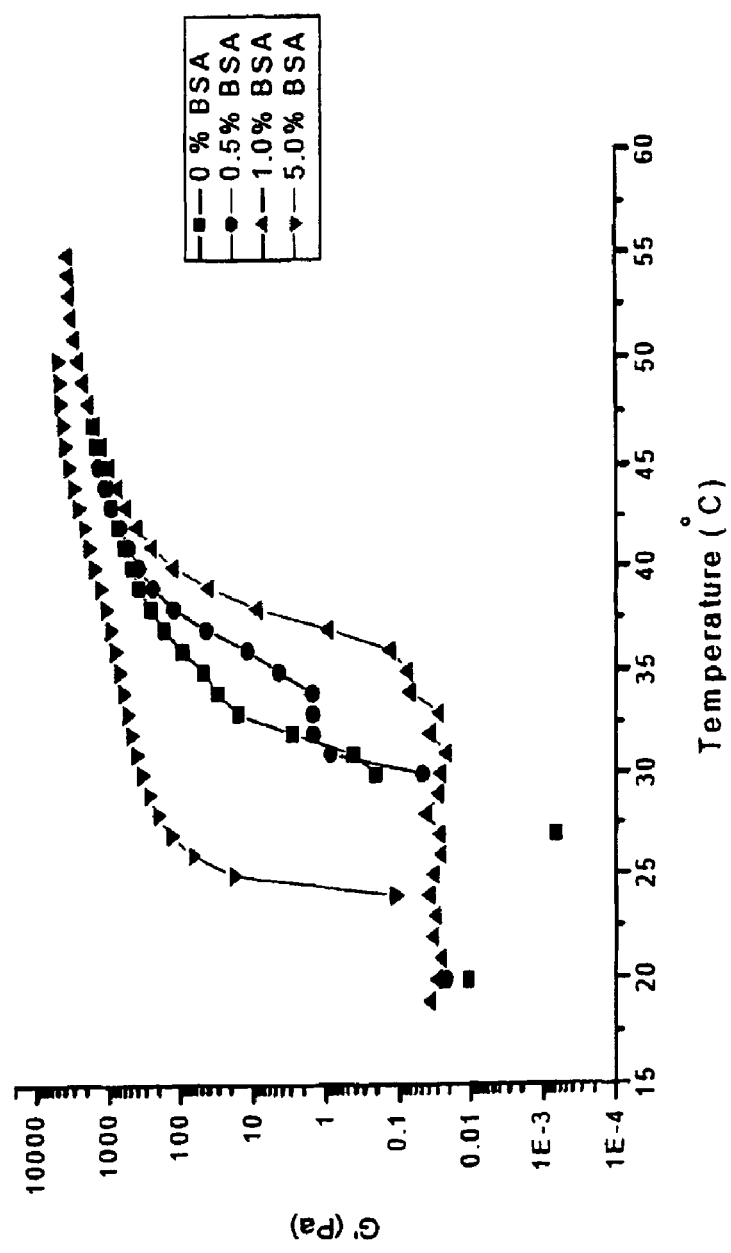
FIG. 7 is a graph of a triblock polymer versus temperature with no protein and three different concentrations of protein added.

A thermoreversible sol-gel which can be used in connection with the present invention is known as poloxamer, also known under the tradename Pluronic® and Lutrol®. Examples of poloxamers include poloxamers 407, 338, 188, and 118. The various pharmaceutical and pharmacological characteristics of poloxamer 407 are described within Dumortier, Pharmaceutical Research, Vol. 23, No. 12, December 2006. Poloxamer 407 is a water soluble block copolymer comprised of poly(ethylene oxide) and poly(propylene oxide). The block polymer component is brought into solution in water. A graph of the modulus of the poloxamer 407 in water (no BSA) over time is shown in FIG. 7 by the line graph with the rectangular data points. FIG. 7 shows that poloxamer 407 undergoes a phase transition between about 25° C. and about 30° C. where the modulus or stiffness of the polymer substantially increases forming the gel. It is contemplated that such a sol-gel composition may be used in the method of the invention, where the sol-gel composition solidifies upon injection into the lumen having a temperature close to the body temperature, for example, 35° C. to 37° C. After the lumens are joined, the gel can be removed by allowing the body fluid to enter the site of ligation and dissolve the gel or by cooling the temperature of the joined lumens to below the transition temperature with, for example, cold saline solution or ice.

In a preferred embodiment of the present invention, the sol-gel composition, such as a poloxamer 407 solution, is modified so as to shift the point at which the composition undergoes a phase change to a higher temperature. Although this can be accomplished by changing the concentration of the polymer in water, if this route is taken it tends to decrease the resulting modulus of the polymer gel formed.

Decreasing the modulus, or elastic modulus (G'), is not desirable for use in connection with the present invention. The compositions useful for this invention should have modulus that is sufficiently high to withstand the pressure applied on the outside of the vessels and to keep the vessels open when the vessels are manipulated during the anastomosis procedure. It is contemplated that the gels of the present invention shall have elastic modulus (G') values of from about 100 to about 500,000 Pascals, and preferably from about 10,000 to about 50,000 Pascals, and more preferably from about 12,000 to about 40,000 Pascals.

Accordingly, it has been contemplated that by the inclusion of another molecule it might be possible to shift the phase transition point in terms of increasing the temperature at which the phase change takes place without decreasing the resulting modulus of the gel formed. It has been found here that by including a transition condition modulating agent which is biocompatible, such as a protein, it is possible to shift the temperature point at which the composition undergoes a phase change.

The data shown in FIG. 7 indicate that Bovine Serum Albumin (BSA) has been added first in a concentration of about 0.5% and then a concentration of about 1.0% and then a concentration of about 5%. The results shown in FIG. 7 indicate that by including the BSA in a composition in an amount of about 1% the phase transition point is shifted so that it occurs at about body temperature or at about 37.5° C.

The resulting composition with about 1% BSA provides a phase transition material which is biocompatible and provides a desirable transition temperature which has been varied without significantly changing the modulus of the resulting gel as compared to the gel without the added BSA.

A preferred formulation is comprised of about 17% polymer such as poloxamer 407, about 1% biocompatible compound such as BSA and about 82% water or a salt solution such as phosphate buffered saline solution. Those skilled in the art will understand that each of these components can be varied in an amount of about ±50%, about ±25%, about ±10%, about ±1% and, depending on the particular polymers and biocompatible compounds used, desirable results may be obtained.

In some embodiments, the biocompatible polymer may have a molecular weight in the range of about 8,000 to 16,000, more preferably 10,000 to 16,000, or more preferably 10,000 to 14,000 and most preferably about 12,600. (As indicated above, the term "about" as used in this context reflects that commercial preparations of the monomers or polymers as described herein may contain mixtures of varying molecular weights incident to the commercial manufacturing process.) That polymer is combined with a biocompatible compound which may be a protein and preferably a protein which does not elicit an immune response. The protein may be a blood protein such as an albumin and specifically may be Bovine Serum Albumin or Human Serum Albumin. (Also as indicated above, recombinant versions of such proteins (or any proteins as described herein) may be preferred for commercial manufacturing reasons, for assurance of no animal-originating pathogenic agents).

In one embodiment, the polymer is present in the composition in an amount of about 15% to 20% by weight, or 16% to 18% by weight or 17% by weight. The polymer is combined with the biocompatible molecule in an amount of about 0.5% to 2% by weight or about 1% by weight. The remainder of the composition is water or phosphate buffered saline. The resulting composition is further characterized by undergoing a phase transition at a temperature higher than the phase transition temperature when the biocompatible compound is not present with a change in modulus of 25% or less, or 10% or less, or 5% or less. More particularly the resulting composition undergoes a phase transition in a relatively narrow range of about 35° C. to about 40° C. or about 36° C. to about 39° C. or more preferably about 37.5° C.

Those skilled in the art will be able to contemplate other phase transition materials which could be used in connection with the invention upon reading this disclosure and examining the data provided. The phase transition may be brought about by a change in condition other than temperature such as a change in pH and those skilled in the art will understand that that pH change may be a change which is brought about at a pH very close to the pH of human blood or a pH of about 7.2.

Presented here is a protocol for a 17% poloxamer 407 with 1% BSA. One of skill in the art may use different concentrations of the thermoreversable material or the protein.

The following materials were mixed together to form 100 ml (100 g) solution of 17% poloxamer 407 with 1% BSA:
  Phosphate buffered saline ("PBS"): 92 g, Gibco #10010, pH 7.4, with $Ca^{2+}$ and $Mg^{2+}$;
  Bovine Serum Albumin ("BSA"): 1 g, Sigma A2153-50 g;
  poloxamer 407: 17 g poloxamer 407, BASF Pluronic® F 127 NF Prill poloxamer 407,
  Material 30085239.

Solutions having 17% poloxamer 407 and 0.1% BSA to 5% BSA were prepared accordingly.

To determine the sol-gel transition temperature (the temperature at which the poloxamer 407 transitions from liquid to gel amounts of each solution were placed between the parallel plates of a stress rheometer (a TA Instruments G2 rheometer was used). The plates were 4 cm in diameter and the gap was set to 1 mm. The elastic modulus was measured using the rheometer at a frequency of 1 Hz and a strain of 0.1 at different temperatures. FIG. 7 is a graph depicting the modulus as a function of temperature. For BSA concentrations at or below 1%, the gelation temperature increased. The gel transition temperature, markedly decreased as the BSA concentration grew from 1% to 5%.

Example 2

Efficacy and Safety in an Animal Model Using Thermoreversible Anastomosis Compositions This working example demonstrates that the present anastomosis compositions are efficacious in joining tubular tissues to result in bodily fluid flow through the resultant continuous lumen.

Anastomosis Using Thermoreversible Gel

Anastomosis was performed in normal rats. The Poloxamer solution in this example refers to the thermoreversible composition containing 17% poloxamer 407 and 1% BSA, as prepared in Example 1, above. All animals are treated and cared for in accordance with all applicable laws and regulations, and in accordance with good laboratory practices.

End to End Anastomosis Surgical Method Performed on Cardiac Tubular Tissues in Rats:

Rats were anesthetized with isoflurane and prepped in sterile fashion with 70% ethanol. The aorta was exposed and isolated with blunt and sharp dissection through a midline laparotomy incision. The aorta was clamped proximally and distally, and subsequently divided and flushed with heparinized saline. In some cases the rat and the poloxamer solution were warmed to 40° C. with sterile water, and then the poloxamer solution was injected in a semi-solid state and in other cases the poloxamer solution was injected into the vessels as a liquid and then heated to 40° C. with a convection source to solidify it. After direct reapproximation by pushing the ends of the aorta together, the cyanoacrylate adhesive was applied and allowed to cure for 60-120 seconds. The clamps were then removed, and the midline incision was closed in layers with 5-0 vicryl (Ethicon, Inc., Somerset, N.J.) and 4-0 nylon (Ethicon) in a running fashion.

End to Side Anastomosis Surgical Method:

Rats were anesthetized, shaved, and prepped in standard sterile fashion. A midline laparotomy incision was made and the abdominal organs eviscerated into a moist 4×4 gauze. The iliac bifurcation was isolated with blunt dissection, and the abdominal aorta was clamped proximally and the iliacs were clamped distally. The left iliac was divided just distal to the bifurcation and an arteriotomy was made in the right iliac. The vessels were then flushed with heparinized saline. The abdomen was warmed at the same time the poloxamer solution was warmed to a gel (about 40° C.) which was then injected. The left iliac was approximated to the right iliac using the sliding clamps (one clamp was on the proximal aorta and the other was on the distal left iliac). Once the ends were opposed without tension, the cyanoacrylate was applied and allowed to set (~5 min). Clamps were then removed and blood flow is restored.

Conventional Handsewn Anastomosis:

Rats were anesthetized, shaved, and prepped in standard sterile fashion. A midline laparotomy incision was made and abdominal organs were eviscerated. The aorta was isolated with blunt dissection and clamped proximally and distally and then divided. The two vessel ends were flushed with heparinized saline. The anastomosis was performed with a running 10-0 nylon suture. Each suture was full thickness through all layers of the aorta. Any areas of leakage were controlled with a simple interrupted suture, and the clamps were removed.

For the end-to-side anastomosis, the iliac bifurcation was isolated as previously described and clamped proximally and distally. The left iliac artery was divided near its origin and reapproximated to the right iliac artery using the clamps. An arteriotomy was made in the right iliac artery and both ends ware flushed with heparinized saline. The anastomosis was then performed with a running 10-0 nylon suture using standard microsurgical techniques and all areas of leakage were controlled with a simple interrupted suture. No successful end-to-side anastomosis were completed with the hand sewn technique.

Results

To evaluate the effectiveness of anastomosis using thermoreversible gel, the patency, flow and burst strength of the vessels connected were measured. The diameters of the anastomotic vessels were measured using conventional CT angiography. Patency and flow were determined through ultrasonic Doppler imaging using a visual sonic machine.

Burst Strength were Determined According to The Following procedure:

Rats were anesthetized and native rat aortas were harvested prior to the operation and operated rat aortas at designated time points postoperatively through a midline laparotomy incision. The aorta was clamped proximally just below the renal arteries and just above the iliac bifurcation. Any small branches were identified and ligated. The harvested aorta was then flushed with saline to remove blood and identify any non-ligated branches. The aorta was then attached to a 22 gauge angiocath using 5-0 silk suture at both ends. The angiocath was equipped with an adapter than attaches directly to the burst strength device. Saline was flushed through the machine and through the aorta at calibrated pressures which were increased incrementally until the anastomosis burst.

Table 1 shows the anastomotic diameters, anastomotic flow, and burst strength of end-to-end anastomotic vessels connected using the thermoreversible sol-gel composition or by handsewing at six weeks post-operation. Patency and survival rate of end-to-end or end-to-side anastomosis using the two methods are compared in Tables 2 and 3.

TABLE 1

End-to-End Anastomosis results*

|  | Time per anastomosis | Anastomotic Diameter | Anastomotic Flow | Burst Strength |
|---|---|---|---|---|
| TRGA group** | Average: 3 min. 11 sec. Range: 55 sec. to 6 min. | 1.93 mm (SD +/− .23 mm) | 75 ml/min (SD +/− 34 ml) | 1345 mmHg (SD +/− 190 mm) |
| handsewn group | Average: 29 min. 15 sec. Range: 20 to 49 min. | 1.23 mm (SD +/− .43 mm) | 63 ml/min (SD +/− 29 ml) | 1248 mmHg (SD +/− 206 mm) |
| p-value |  | 0.027 | not significant | not significant |

*Preliminary results at six weeks
**Thermoreversible gel anastomosis group

TABLE 2

End-to-End Anastomosis results*

| Procedure used | Number of rats | Patency Rate among survivors | Number and causes of deaths |
|---|---|---|---|
| TRGA | n = 26 | 100% | One early anesthetic death. |
| Hand-sewn | n = 25 | 86% | Three early deaths from perioperative leak and hemorrhage; Two late deaths; Two distal ischemic events requiring sacrifice. |

TABLE 3

Side-to-End Anastomosis results*

| Procedure used | Number of rats | Patency Rate among survivors | Number and causes of deaths |
|---|---|---|---|
| TRGA | n = 13 | 100% | No deaths or ischemic events. |
| Hand-sewn | n = 10 | 10% | 60% with significant limb ischemia requiring sacrifice; One patent anastomosis occluded ipsilateral iliac at "toe". |

Example 3

Figure 8:
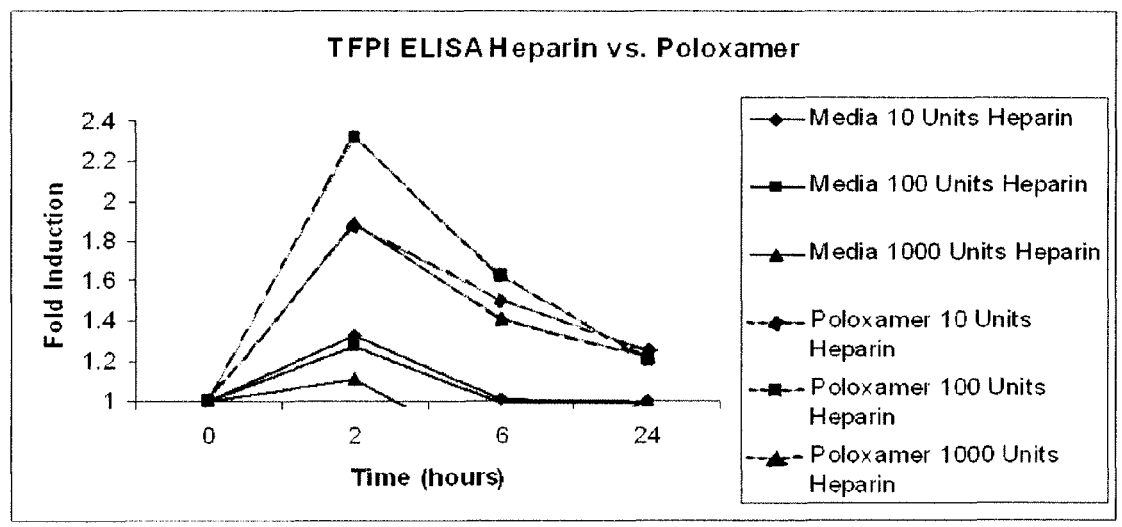
FIG. 8 is a graph of the effect of heparin delivered with poloxamer as compared with heparin delivered directly.

Use of Reversible Gel-Sol Anastomosis Compositions for Sustained Delivery of a Biologically Functional Molecule The present materials were used for delivery of heparin, as determined by an enzyme linked immunoadsorbent assay. The present thermoreversible sol-gel composition containing heparin was compared to media alone. Human umbilical vein endothelial cells were incubation for 5 minutes in trans-well plates. Heparin in varied concentrations (10, 100 and 1000 U/mL) were added to the cells directly or with poloximer. Tissue Factor Pathway Inhibitor (TFPI), tissue factor (TF), thrombomodulin (TM) were measured at 2 hr, 6 hr and 24 hr post heprin addition using a ELISA kit (R&D Systems, MN USA). As shown in FIG. 8, poloxamer-mediated delivery of heparin is more effective than direct administration of heparin. Further, the effects of heparin persist up to 24 hours with poloxamer mediated delivery, longer than with direct administration. This demonstrates that as the composition transitions from gel to liquid, the heparin is released for a sustained release effect.

The following Examples 4-7 are prophetic and have not yet been conducted. Rather these examples define methods which are readily correlated from Examples 1-3 and 8 which were actually performed.

Example 4

Prophetic Example of Use of Wax Compositions in an Anastomosis Procedure

This prophetic example illustrates the use of a wax composition as the solid mass to provide structural support for a lumen during anastomosis. It is contemplated that the treated mammal will be anesthetized with isoflurane and prepped in sterile fashion with 70% ethanol. The aorta is exposed and clamped proximally and distally, and subsequently divided and flushed with heparinized saline. After being cut and flushed with saline, the temperature of the divided aorta becomes slightly lower than that of the body temperature. A wax composition having a melting point at about the normal rat body temperature, for example, a mixture of capric acid and lauric acid, is placed in the two open ends of the divided aorta in a matter to maintain the structural integrity of the aorta. After direct reapproximation by pushing the ends of the aorta together, the cyanoacrylate adhesive is applied and allowed to cure for 60-120 seconds. The clamps are then removed to allow blood to flow to the anastomosis point, causing the temperature to rise to about body temperature, which is sufficient to melt the wax composition and establish blood flow through the entire aorta.

In another example, a wax composition having a melting point slightly higher than the body temperature is preformed into a "stick" configuration of a diameter similar to that of the above aorta. The stick is inserted to one end of the aorta in a manner that a portion of the stick protrudes outside the aorta. The protruding portion of the stick is then inserted into the other end of the aorta so that the two ends are brought together. The cyanoacrylate adhesive is applied and allowed to cure for 60-120 seconds. The anastomosis point is warmed up to the melting point of the wax to melt the wax stick inside the aorta. The clamps are then removed to allow blood flow to be restored.

Example 5

Prophetic Example of Use of Thermoreversible Sol-Gel Compositions for a Vavovasectomy This prophetic example illustrates how the present invention could be used to connect tubular tissues which do not need immediate restoration of body fluid flow, but rather may benefit from a gradual healing, and therefore, a slower degradation of the subject sol-gel material in situ. A patient desires a vavovasectomy to reverse a vasectomy. The practitioner locates the previously cut vas deferens termini, and re-cuts a portion to open the tubular tissue lumen. A sol-gel composition of pasty texture is placed into the termini of each portion of the vas deferens, thereby stabilizing the tubular geometry. The stabilized termini are matched up, and meth-acrylate or other bio adhesive is applied and allowed to cure, if appropriate. The sol-gel composition does not immediately liquefy, but gradually biodegrades into constituent moieties which are absorbed by the surrounding tissue. The sol-gel optionally locally delivers in a sustained release fashion wound healing or anti-inflammatory biologically functional moieties, so that the now-reattached vas deferens does not occlude or become re-blocked due to scar tissue or undue inflammatory response.

The procedure described above may be used in other surgical procedures to remove blockage of other tubular tissues. It is contemplated that a dye may be incorporated into the wax composition for easy alignment of the non-conjoined lumens, especially for a lumen having a thick wall where the lumen is difficult to see.

Example 6

Prophetic Example of Use of Sol-Gel Material and Adhesive Ligation

This prophetic example illustrates an example of initiation of anastomosis using a photoinitiation solidification and an enzymatically-initiated liquefication using a sol-gel composition engineered to have photoactivatable cross-linking initiation sites, and enzyme-recognitions site for biodegradation. The sol-gel transitions toward solid upon exposure to the appropriate wavelength of light, and transitions toward liquid upon exposure to the enzyme, (or becomes more liquid) and dissolves into the systemic circulation, for example. A practitioner deploys the substantially liquid sol-gel to the terminus of a first tubular tissue, and applies a suitable wavelength of light for substantially solidifying the sol-gel. If the tubular tissue is in vivo, the light may be applied using fiber optic means, or if the tubular tissue is ex vivo, a suitable light source may be applied. The polymeric backbone of the sol-gel may be engineered to include an enzyme recognition site, such as a protease recognition site. The practitioner matches up the termini of the tubular tissue, and applies adhesive externally to the seam where the termini adjoin, and allows the sealant to cure, thereby creating a contiguous tubular tissue. Enzyme is injected into the location of the substantially solidified sol-gel and the sol-gel is digested into constituent parts, which are then absorbed by surrounding tissue or removed as part of the systemic body waste removal.

Example 7

Prophetic Example of Use of A Sol-Gel Material Having a Transition Temperature at or Below the Body Temperature in a End-to-End Anastomosis The aorta of a patient in need of the procedure is clamped proximally and distally, and subsequently divided and flushed with heparinized saline. A sol-gel composition having a transition temperature at or below the body temperature, e.g. at about 15° C. to about 30° C., is injected in a semi-solid or a gel state. The sol-gel composition may contain about 5% to about 30% of a poloxamer. For example, the composition of 17% Poloxamer 407 in water has a transition temperature of 25° C. to 30° C. as shown in FIG. 7. As such, Poloxamer 407 solidifies when injected into the aorta which has a temperature of above 30° C. After direct reapproximation by pushing the ends of the aorta together, the cyanoacrylate adhesive is applied and allowed to cure for 60-120 seconds. An appropriate amount of cold sterile saline or ice is applied to the sited connected to induce the gel change to a liquid. The clamps are then removed to reestablish blood flow, and the midline incision is closed in layers with 5-0 vicryl (Ethicon, Inc., Somerset, N.J.) and 4-0 nylon (Ethicon) in a running fashion.

Example 8

An Anastomosis Operation Using a Sol-Gel Composition with Two Poloxamers

Methods: Rheological studies as described in Example 1 determined the formulation of 17% of poloxamer 407 and 6% of poloxamer 188 (P407/P188) could obtain a phase transition temperature at 42° C. Anastomoses were performed on Fisher rat aortas using P407/P188 and bioadhesives (n=30) and 10-0 nylon sutures (n=30). CT angiograms, burst strength assays, histology, and scanning electron microscopy (SEM) were performed at designated timepoints. Tissue factor pathway inhibitor (TFPI) ELISA was performed on media harvested from human umbilical vein endothelial cells (HUVECs) exposed to heparin and heparinized P407/P188.

Results: The average diameter of the rat aorta used for the end-to-end anastomoses in this study was 2.8 mm, and the average diameter of the iliac vessels used in the end-to-side anastomoses was 1.9 mm. End-to-end anastomoses performed using P407/P188 were completed more efficiently than the hand-sewn technique ($10.0\pm4.2$ min vs. $47.3\pm5.0$ min, $p<0.05$) with equivalent burst strengths (>1500 mm Hg, $p>0.05$). Angiograms demonstrated equivalent patency, and flow through native aorta, hand-sewn anastomoses, and sutureless anastomoses were not significantly different (26 mL/sec vs. 27 mL/sec vs. 29 mL/sec respectively). Histology and SEM demonstrated less fibrosis in the sutureless group compared with the traditional technique. End-to-side anastomoses performed with the hand-sewn technique had 100% failure rate; however, end-to-side sutureless anastomoses were successful in 33% of operations performed ($p<0.05$). Heparinized poloxamer-induced a significant percentage increase in secretion of TFPI compared with heparin administered directly to HUVECs (231.8%, $p<0.05$) with effects lasting up to 24 hours (125.4%, $p<0.05$).

The results indicates that P407/P188 can provide an efficient and sustained means of delivering antithrombotic agents, and sutureless anastomoses achieve equivalent patency rates and burst strength with significantly less fibrosis. This technology has promising implications for the fields of vascular, cardiothoracic, plastic, and transplant surgery.

Example 9

Prophetic Example of Using a Sol-Gel Composition in a Vascular Grafting Procedure In clinical practice, there are some instances where native vessels (i.e. blood vessels of the patient) are not available for bypass grafting or where, especially for older patients, native fistulas require a long maturation time or do not develop sufficiently. In these instances, physicians may choose to use artificial conduits such as grafts comprising polytetrafluoroethylene (PTFE), which can be formed in reinforced or non-reinforced configurations, for example expended PTFE (ePTFE) grafts, manufactured by Gore and others. Synthetic internal arteriouvenous (AV) fistulas or AV grafts, can be placed in many positions in the arms or legs or across the anterior chest wall.

The artificial grafts may be used instead of native vessels in all configurations: end-to-end inter-positional grafting, end-to-side for procedures such as artery to vein shunt for dialysis fistula access, end-to-side bypass procedure both for coronary bypass as well as peripheral bypass. For example, in the below the knee bypass, the graft is attached proximally to the femoral artery and then distally to the popliteal artry and this conduit carries the blood to the distal limb. The procedure for using the graft is similar to the ones for native vessels described above, where the ends of the non-conjoined lumen (expect here one native and one graft) are filled with the gel, followed by alignment of the ends, depositing of glue over the joint, dissolution of the gel is dissolved to complete the anastomosis.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for joining at least two non-conjoined lumens in a patient, wherein at least one of the lumens has a clamp to arrest the flow of the fluid therein, which method comprises:
    (a) placing a biocompatible sol-gel composition by injection with a hypodermic needle and/or a syringe in a liquid phase or a gel phase in at least a distal portion of the lumen having the clamp, wherein when the sol-gel composition is placed in the lumen in the liquid phase, a phase transition is induced wherein the liquid phase changes to the gel phase, and wherein the gel phase of the sol-gel composition provides structural support to said portion of the lumen;
    (b) aligning the lumens;
    (c) closing the aligned lumens to form a conduit;
    (d) inducing a phase change of the biocompatible sol-gel composition from the gel phase to the liquid phase;
    (e) confirming substantial completion of the phase change; and
    (f) removing the clamp thereby establishing flow through the conduit.

2. The method of claim 1, wherein the biocompatible sol-gel composition is placed in the distal portion of each lumen to be joined.

3. The method of claim 1, wherein the biocompatible sol-gel composition is placed in the distal portion of a first lumen in a manner in which the biocompatible sol-gel composition protrudes from the distal portion such that this protrusion can be used as a male-mating functionality with the distal portion of the second lumen which acts as a female-mating functionality.

4. The method of claim 1, wherein the phase change of the biocompatible sol-gel composition comprises melting, phase change triggered by a stimulus, change in viscosity, or combinations thereof.

5. The method of claim 1, wherein the biocompatible sol-gel composition is placed in the lumen in the gel phase.

6. A method for joining at least two non-conjoined lumens in a patient, which method comprises:
   (a) approximating the lumens in a connecting position;
   (b) providing a biocompatible phase-reversible sol-gel composition in a gel phase in the distal portion of both lumens by injection with a hypodermic needle and/or a syringe;
   (c) closing the lumens to form a conduit;
   (d) inducing a phase transition of the sol-gel composition wherein the sol-gel composition changes from the gel phase to a liquid phase; and
   (e) establishing flow through the conduit.

7. The method of claim 6, further comprises a step before step (a), which step comprises arresting the flow of body fluid in the lumens.

8. The method of claim 7, wherein the arresting the flow of body fluid in the lumen comprises clamping at least one of the lumens.

9. The method of claim 8, wherein step (e) comprises (e1) observing the conduit to confirm substantial completion of the phase transition, and (e2) removing the clamps thereby establishing flow through the conduit and removing the sol-gel composition.

10. The method of claim 7, wherein the arresting the flow of body fluid in the lumen comprises applying a pressure on at least one of the lumens.

11. The method of claim 6, wherein the approximating the lumens in a connecting position comprises partially suturing the lumens.

12. The method of any one of claims 1, 5 and 8, further comprising flushing the distal potion of the clamped lumen with a biocompatible liquid prior to step (a).

13. The method of claim 1, 5, or 6, wherein joining of the lumens comprises suturing, applying a biocompatible adhesive, applying laser, electrocautery or combinations thereof 14. The method of claim 13, wherein joining of the lumens comprises using a biocompatible adhesive.

15. The method of claim 13, wherein joining of the lumen comprises a combination of suturing and applying a biocompatible adhesive.

16. The method of claim 13, wherein the biocompatible adhesive is selected from among a cyanoacrylate-based adhesive, a fibrin-based adhesive, a polyurethane-based adhesive, a latex glue, a biologics glue, a polyethylene glycol-based glue, and a polyisocyanate-based adhesive.

17. A method for joining at least two non-conjoined lumens in a patient, wherein at least one of the lumens is clamped to arrest the flow of body fluid therein, which method comprises:
   flushing the distal potion of the clamped lumen with a biocompatible liquid;
   approximating the lumens in a connecting position, which approximating comprises partially suturing the lumens;
   providing a biocompatible phase-reversible sol-gel composition in a gel phase in the distal portion of both lumens by injection with a hypodermic needle and/or a syringe;
   closing the lumens to form a conduit with a biocompatible adhesive;
   inducing a phase transition of the sol-gel composition wherein the sol-gel composition changes from the gel phase to a liquid phase;
   confirming substantial completion of the phase transition; and
   removing the clamps thereby establishing flow through the conduit.

18. The method of claim 17, wherein the sol-gel composition has an elastic modulus of at least 8,000 Pascals when in the gel phase.

19. The method of any one of claims 5, 6 and 17, wherein the phase-transition of the sol-gel composition is triggered by a stimulus selected from a change in temperature, a change in pH, a change in ionic strength, a change in pressure, a change in electric field, a change in magnetic field, a change in electron magnetic radiation, a change in light or ultraviolet light, a change in concentration, a change in osmolarity, and combinations thereof.

20. The method of any one of claims 5, 6 and 17, wherein the sol-gel composition has an elastic modulus of at least 100 Pascals when in the gel phase.

21. The method of any one of claims 5, 6 and 17, wherein the sol-gel composition is a thermoreversible sol-gel having a transition temperature of from about 0° C. to about 45° C.

22. The method of claim 21, wherein the sol-gel is maintained in the gel phase by applying a heat source and changed from the gel phase to the liquid phase by removing the heat source.

23. The method of claim 21, wherein the sol-gel is changed from the gel phase to the liquid phase by cooling the joined lumens to a temperature that is below the transition temperature of the sol-gel composition.

24. The method of claim 21, wherein the thermoreversible sol-gel comprises an aqueous solvent and a polymer selected from the group consisting of poloxamer 118, poloxamer 188, poloxamer 338, poloxamer 407, Tetronic® 1107 and Tetronic® 1307, or a mixture thereof.

25. The method of claim 24, wherein the polymer is present in an amount of about 5% to about 35% by weight.

26. The method of any one of claims 5, 6 and 17, wherein the phase-transition of the sol-gel composition is triggered by a stimulus which comprises a change in ionic strength.

27. The method of any one of claims 1, 6, and 17, wherein the lumens are each independently selected from the group consisting of a vessel of the cardiovascular system of the patient human, an arteriovenous graft and an arteriovenous shunt.

28. A method for imaging the joinder of at least two non-conjoined lumens using a method of any one of claims 1, 6, and 17, comprising:
   (a) acquiring an image of the sol-gel composition in the lumen; and
   (b) acquiring an image showing alignment of the lumens and closure of the aligned lumens to form a conduit.

29. A method for visualizing guidance of the joinder of at least two non-conjoined lumens using a method of any one of claims 1, 6, and 17, comprising:
   (a) displaying the placement of the sol-gel composition in the lumen in proper position to provide structural support for the lumen;
   (b) visualizing the proper alignment of the lumens to be joined;
   (c) visualizing the closing of the lumens to form a conduit; and
   (d) visualizing the induction of the phase change of the sol-gel composition in the lumen where the sol-gel composition changes from the gel phase to the liquid phase.

30. A method for evaluating the effectiveness of a method for joining at least two non-conjoined lumens in a patient using a method of any one of claims 1, 6, and 17, comprising:
- (a) measuring the serum concentration of biomarkers indicative of myocardial performance or the performance of other organs connected to the conjoined lumens; and/or
- (b) measuring the diameters of the conjoined lumens; and/or
- (c) determining patency and flow; and/or
- (d) monitoring the presence of the flowable liquid in the serum or urine.

* * * * *